(12) United States Patent
Luettgen et al.

(10) Patent No.: US 9,642,677 B2
(45) Date of Patent: May 9, 2017

(54) ORAL IRRIGATOR WITH MASSAGE MODE

(71) Applicant: Water Pik, Inc., Fort Collins, CO (US)

(72) Inventors: Harold A. Luettgen, Windsor, CO (US); Gordon Haszier, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 734 days.

(21) Appl. No.: 13/831,401

(22) Filed: Mar. 14, 2013

(65) Prior Publication Data

US 2014/0272782 A1    Sep. 18, 2014

(51) Int. Cl.
| | | |
|---|---|---|
| *A61H 13/00* | (2006.01) | |
| *A61C 17/02* | (2006.01) | |
| *A61C 1/00* | (2006.01) | |
| *A61C 17/028* | (2006.01) | |

(52) U.S. Cl.
CPC .......... *A61C 1/0092* (2013.01); *A61C 1/0015* (2013.01); *A61C 17/0205* (2013.01); *A61C 17/028* (2013.01); *A61H 13/005* (2013.01)

(58) Field of Classification Search
CPC ..... A61C 17/00; A61C 17/02; A61C 17/0202; A61C 17/0205; A61C 17/028
See application file for complete search history.

(56) References Cited

U.S. PATENT DOCUMENTS

| | | |
|---|---|---|
| 555,588 A | 3/1896 | Spencer |
| 1,278,225 A | 9/1918 | Schamberg |
| 1,464,419 A | 8/1923 | Gill |
| 1,498,267 A | 6/1924 | Nachman |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 2,107,686 A | 2/1938 | Bramsen et al. |
| 2,230,238 A | 2/1941 | Duberstein et al. |
| 2,417,759 A | 3/1947 | Johnson |
| 2,669,233 A | 2/1954 | Friend |
| 2,794,437 A | 6/1954 | Tash |
| 2,783,919 A | 3/1957 | Ansell |
| 2,870,932 A | 1/1959 | Davis |

(Continued)

FOREIGN PATENT DOCUMENTS

| | | |
|---|---|---|
| CA | 851479 | 9/1970 |
| CH | 655237 | 4/1987 |

(Continued)

OTHER PUBLICATIONS

US RE27,274, 01/1972, Mattingly (withdrawn)

(Continued)

*Primary Examiner* — Justine Yu
*Assistant Examiner* — Michael Tsai
(74) *Attorney, Agent, or Firm* — Dorsey & Whitney LLP

(57) ABSTRACT

An irrigating device, such as an oral irrigator or a nasal irrigator. The irrigating device includes a pump and a motor connected to the pump and configured to selectively drive the pump. Additionally, the irrigating device includes a massage module in communication with the motor. During a normal mode, the pump has a first pulse rate and during a massage mode, the massage module provides a massage control signal to the motor, causing the pump to have a second pulse rate.

27 Claims, 17 Drawing Sheets

(56) References Cited

U.S. PATENT DOCUMENTS

| | | | |
|---|---|---|---|
| 2,984,452 A | 5/1961 | Hooper | |
| 3,089,490 A | 5/1963 | Goldberg | |
| 3,096,913 A | 7/1963 | Jousson | |
| 3,144,867 A | 8/1964 | Trupp et al. | |
| 3,209,956 A | 10/1965 | McKenzie | |
| 3,216,619 A | 11/1965 | Richards et al. | |
| 3,225,759 A | 12/1965 | Drapen et al. | |
| 3,227,158 A | 1/1966 | Mattingly | |
| 3,266,623 A | 8/1966 | Poferl | |
| 3,297,558 A | 1/1967 | Hillquist | |
| D208,778 S | 10/1967 | Koch | |
| D209,204 S | 11/1967 | St. Clair et al. | |
| D209,395 S | 11/1967 | Gilbert | |
| D210,018 S | 1/1968 | Mattingly et al. | |
| D210,019 S | 1/1968 | Johnson et al. | |
| 3,370,214 A | 2/1968 | Aymar | |
| 3,391,696 A | 7/1968 | Woodward | |
| 3,393,673 A | 7/1968 | Mattingly et al. | |
| 3,400,999 A | 9/1968 | Goldstein | |
| 3,418,552 A | 12/1968 | Holmes | |
| 3,420,228 A | 1/1969 | Kalbfeld | |
| 3,425,410 A | 2/1969 | Cammack | |
| 3,453,969 A | 7/1969 | Mattingly | |
| 3,465,751 A | 9/1969 | Powers | |
| 3,467,083 A | 9/1969 | Mattingly | |
| 3,487,828 A | 1/1970 | Troy | |
| 3,489,268 A | 1/1970 | Meierhoefer | |
| 3,495,587 A | 2/1970 | Freedman | |
| 3,496,933 A | 2/1970 | Lloyd | |
| 3,499,440 A | 3/1970 | Gibbs | |
| 3,500,824 A | 3/1970 | Gilbert | |
| 3,501,203 A | 3/1970 | Falk | |
| 3,502,072 A | 3/1970 | Stillman | |
| 3,517,669 A | 6/1970 | Buono et al. | |
| D218,270 S | 8/1970 | Soper | |
| 3,522,801 A | 8/1970 | Robinson | |
| 3,532,221 A | 10/1970 | Kaluhiokalani et al. | |
| 3,536,065 A | 10/1970 | Moret | |
| 3,537,444 A | 11/1970 | Garn | |
| 3,538,950 A | 11/1970 | Porteners | |
| 3,547,110 A | 12/1970 | Balamuth | |
| 3,561,433 A | 2/1971 | Kovach | |
| D220,334 S | 3/1971 | Mackay et al. | |
| 3,570,525 A | 3/1971 | Borsum et al. | |
| 3,572,375 A | 3/1971 | Rosenberg | |
| 3,578,884 A | 5/1971 | Jacobson | |
| 3,583,609 A | 6/1971 | Oppenheimer | |
| 3,590,813 A | 7/1971 | Roszyk | |
| 3,608,548 A | 9/1971 | Lewis | |
| D222,862 S | 1/1972 | Cook | |
| 3,636,947 A | 1/1972 | Balamuth | |
| 3,651,576 A | 3/1972 | Massa | |
| 3,669,101 A | 6/1972 | Kleiner | |
| 3,703,170 A | 11/1972 | Ryckman, Jr. | |
| 3,747,595 A | 7/1973 | Grossan | |
| 3,768,472 A | 10/1973 | Hodosh et al. | |
| 3,783,364 A | 1/1974 | Gallanis et al. | |
| 3,809,506 A | 5/1974 | Malcosky | |
| 3,809,977 A | 5/1974 | Balamuth et al. | |
| 3,811,432 A | 5/1974 | Moret | |
| 3,820,532 A | 6/1974 | Eberhardt et al. | |
| 3,827,147 A | 8/1974 | Condon | |
| 3,837,166 A | 9/1974 | Hiraoka | |
| 3,840,795 A | 10/1974 | Roszyk et al. | |
| 3,847,145 A | 11/1974 | Grossan | |
| 3,854,209 A | 12/1974 | Franklin et al. | |
| 3,863,628 A * | 2/1975 | Vit | A61C 17/028 433/216 |
| 3,874,506 A | 4/1975 | Hill et al. | |
| 3,881,868 A | 5/1975 | Duke | |
| 3,898,739 A | 8/1975 | Gayso | |
| 3,912,125 A | 10/1975 | Acklin | |
| 3,943,628 A | 3/1976 | Kronman et al. | |
| 3,959,883 A | 6/1976 | Walls et al. | |
| 3,973,558 A | 8/1976 | Stouffer et al. | |
| 3,977,084 A | 8/1976 | Sloan | |
| 4,001,526 A | 1/1977 | Olson | |
| 4,004,302 A | 1/1977 | Hori | |
| 4,007,739 A | 2/1977 | Bron et al. | |
| 4,052,002 A | 10/1977 | Stouffer et al. | |
| D246,667 S | 12/1977 | Mackay et al. | |
| 4,060,870 A | 12/1977 | Cannarella | |
| 4,075,761 A | 2/1978 | Behne et al. | |
| 4,078,558 A | 3/1978 | Woog et al. | |
| 4,089,079 A | 5/1978 | Nicholson | |
| 4,108,167 A | 8/1978 | Hickman et al. | |
| 4,108,178 A | 8/1978 | Betush | |
| 4,109,650 A | 8/1978 | Peclard | |
| 4,122,845 A | 10/1978 | Stouffer et al. | |
| 4,135,501 A | 1/1979 | Leunissan | |
| 4,141,352 A | 2/1979 | Ebner et al. | |
| 4,144,646 A | 3/1979 | Takemoto et al. | |
| 4,149,315 A | 4/1979 | Page, Jr. et al. | |
| 4,154,375 A | 5/1979 | Bippus | |
| 4,160,383 A | 7/1979 | Rauschenberger | |
| 4,182,038 A | 1/1980 | Fleer | |
| 4,201,200 A | 5/1980 | Hubner | |
| 4,215,476 A | 8/1980 | Armstrong | |
| 4,219,618 A | 8/1980 | Leonard | |
| 4,227,878 A | 10/1980 | Lohn | |
| 4,229,634 A | 10/1980 | Hickman et al. | |
| 4,236,889 A | 12/1980 | Wright | |
| 4,248,589 A | 2/1981 | Lewis | |
| 4,249,899 A | 2/1981 | Davis | |
| 4,257,458 A | 3/1981 | Kondo et al. | |
| 4,262,799 A | 4/1981 | Perrett | |
| 4,266,934 A | 5/1981 | Pernot | |
| 4,276,023 A | 6/1981 | Phillips et al. | |
| 4,276,880 A | 7/1981 | Malmin | |
| 4,302,186 A | 11/1981 | Cammack et al. | |
| 4,303,064 A | 12/1981 | Buffa | |
| 4,303,070 A | 12/1981 | Ichikawa et al. | |
| 4,315,741 A | 2/1982 | Reichl | |
| 4,319,568 A | 3/1982 | Tregoning | |
| 4,331,422 A | 5/1982 | Heyman | |
| 4,337,040 A | 6/1982 | Cammack et al. | |
| 4,340,365 A | 7/1982 | Pisanu | |
| 4,340,368 A | 7/1982 | Lococo | |
| D266,117 S | 9/1982 | Oberheim | |
| 4,353,694 A | 10/1982 | Pelerin | |
| 4,363,626 A | 12/1982 | Schmidt et al. | |
| 4,365,376 A | 12/1982 | Oda et al. | |
| 4,370,131 A | 1/1983 | Banko | |
| 4,374,354 A | 2/1983 | Petrovic et al. | |
| 4,382,167 A | 5/1983 | Maruyama et al. | |
| 4,382,786 A | 5/1983 | Lohn et al. | |
| D270,000 S | 8/1983 | Ketler | |
| 4,412,823 A | 11/1983 | Sakai et al. | |
| 4,442,830 A | 4/1984 | Markau | |
| 4,442,831 A | 4/1984 | Trenary | |
| 4,452,238 A | 6/1984 | Kerr | |
| 4,454,866 A | 6/1984 | Fayen | |
| 4,512,769 A | 4/1985 | Kozam et al. | |
| 4,517,962 A | 5/1985 | Heckele | |
| 4,531,912 A | 7/1985 | Schuss et al. | |
| 4,531,913 A | 7/1985 | Taguchi | |
| 4,534,340 A | 8/1985 | Kerr et al. | |
| 4,552,130 A | 11/1985 | Kinoshita | |
| 4,561,214 A | 12/1985 | Inoue | |
| D283,374 S | 4/1986 | Cheuk-Yiu | |
| 4,585,415 A | 4/1986 | Hommann | |
| 4,591,777 A | 5/1986 | McCarty et al. | |
| 4,592,728 A | 6/1986 | Davis | |
| 4,602,906 A | 7/1986 | Grunenfelder | |
| 4,607,627 A | 8/1986 | Leber et al. | |
| 4,613,074 A | 9/1986 | Schulze | |
| 4,619,009 A | 10/1986 | Rosenstatter | |
| 4,619,612 A | 10/1986 | Weber et al. | |
| 4,629,425 A | 12/1986 | Detsch | |
| 4,636,198 A | 1/1987 | Stade | |
| 4,642,037 A | 2/1987 | Fritchman | |
| 4,644,937 A | 2/1987 | Hommann | |
| 4,645,488 A | 2/1987 | Matukas | |
| 4,647,831 A | 3/1987 | O'Malley et al. | |

(56) References Cited

U.S. PATENT DOCUMENTS

| | | |
|---|---|---|
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kandler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,331,704 A | 7/1994 | Rosen et al. |
| 5,344,317 A * | 9/1994 | Pacher .................. A61C 17/02 433/100 |
| 5,346,677 A | 9/1994 | Risk |
| D351,892 S | 10/1994 | Wolf et al. |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,467,495 A | 11/1995 | Boland et al. |
| 5,468,148 A | 11/1995 | Ricks |
| 5,470,305 A | 11/1995 | Arnett et al. |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,014 A | 9/1996 | Becker |
| 5,554,025 A | 9/1996 | Kinsel |
| 5,556,001 A | 9/1996 | Weissman et al. |
| 5,564,629 A | 10/1996 | Weissman et al. |

(56) References Cited

U.S. PATENT DOCUMENTS

| | | |
|---|---|---|
| D377,091 S | 12/1996 | Scott, Sr. |
| 5,616,028 A | 4/1997 | Hafele et al. |
| 5,626,472 A | 5/1997 | Pennetta |
| 5,634,791 A | 6/1997 | Matsuura et al. |
| 5,636,987 A | 6/1997 | Serfaty |
| 5,640,735 A | 6/1997 | Manning |
| 5,653,591 A | 8/1997 | Loge |
| 5,659,995 A | 8/1997 | Hoffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| 5,709,545 A | 1/1998 | Johnston et al. |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,654 A | 7/1998 | Foley et al. |
| 5,795,153 A | 8/1998 | Rechmann |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,934,902 A | 8/1999 | Abahusayn |
| D413,975 S | 9/1999 | Maeda |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| 6,041,462 A | 3/2000 | Marques |
| 6,047,429 A | 4/2000 | Wu |
| D425,615 S | 5/2000 | Bachman et al. |
| D425,981 S | 5/2000 | Bachman et al. |
| 6,056,710 A | 5/2000 | Bachman et al. |
| D426,633 S | 6/2000 | Bachman et al. |
| 6,089,865 A | 7/2000 | Edgar |
| 6,116,866 A | 9/2000 | Tomita et al. |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,230,717 B1 | 5/2001 | Marx et al. |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,247,929 B1 | 6/2001 | Bachman et al. |
| D448,236 S | 9/2001 | Murray |
| 6,293,792 B1 | 9/2001 | Hanson |
| D449,884 S | 10/2001 | Tobin et al. |
| D453,453 S | 2/2002 | Lun |
| 6,363,565 B1 | 4/2002 | Paffrath |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,558,344 B2 | 5/2003 | McKinnon et al. |
| 6,561,808 B2 | 5/2003 | Neuberger |
| D475,346 S | 6/2003 | McCurrach et al. |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,669,059 B2 | 12/2003 | Mehta |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| 7,131,838 B2 * | 11/2006 | Suzuki .................. A61C 17/02 433/80 |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| 7,500,584 B2 | 3/2009 | Schutz |
| D590,492 S | 4/2009 | Powell |
| D595,136 S | 6/2009 | Canamasas Puigbo |
| D601,697 S | 10/2009 | Sobiech et al. |
| D603,708 S | 11/2009 | Handy |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |

(56) References Cited

U.S. PATENT DOCUMENTS

| | | |
|---|---|---|
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,878,403 B2 | 2/2011 | Hennick et al. |
| 7,959,597 B2 | 6/2011 | Baker et al. |
| D640,872 S | 7/2011 | Nanda |
| D648,539 S | 11/2011 | Wai |
| D651,805 S | 1/2012 | Hay |
| 8,113,832 B2 | 2/2012 | Snyder et al. |
| D658,381 S | 5/2012 | Gebski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| 8,366,024 B2 | 2/2013 | Leber et al. |
| 8,403,577 B2 | 3/2013 | Khoshnevis |
| 8,403,665 B2 | 3/2013 | Thomas et al. |
| 8,408,483 B2 | 4/2013 | Boyd et al. |
| D694,398 S | 11/2013 | Taylor |
| D707,350 S | 6/2014 | Woodard |
| 8,801,667 B2 | 8/2014 | Taylor |
| D717,427 S | 11/2014 | Kim |
| D731,640 S | 6/2015 | Kim et al. |
| 9,050,157 B2 | 6/2015 | Boyd et al. |
| D747,464 S | 1/2016 | Taylor |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2003/0098249 A1 | 5/2003 | Rollock |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0209222 A1 | 10/2004 | Snyder |
| 2005/0004498 A1 | 1/2005 | Klupt |
| 2005/0049620 A1 | 3/2005 | Chang |
| 2005/0064371 A1 | 3/2005 | Soukos et al. |
| 2005/0101894 A1 | 5/2005 | Hippensteel |
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0008373 A1 | 1/2006 | Schutz |
| 2006/0010624 A1 | 1/2006 | Cleland |
| 2006/0021165 A1 | 2/2006 | Boland et al. |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2007/0082316 A1 | 4/2007 | Zhadanov et al. |
| 2007/0113360 A1 | 5/2007 | Tsai |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0008979 A1* | 1/2008 | Thomas ............ A61C 17/0202 433/80 |
| 2008/0189951 A1* | 8/2008 | Molema ................. B26B 19/40 30/41 |
| 2008/0307591 A1 | 12/2008 | Farrell et al. |
| 2009/0070949 A1 | 3/2009 | Sagel et al. |
| 2009/0082706 A1 | 3/2009 | Shaw |
| 2009/0124945 A1 | 5/2009 | Reich et al. |
| 2009/0163839 A1 | 6/2009 | Alexander |
| 2009/0281454 A1 | 11/2009 | Baker et al. |
| 2010/0010524 A1 | 1/2010 | Barrington |
| 2010/0015566 A1 | 1/2010 | Shaw |
| 2010/0190132 A1 | 7/2010 | Taylor et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2012/0021374 A1 | 1/2012 | Cacka et al. |
| 2012/0045730 A1 | 2/2012 | Sayder et al. |
| 2012/0064480 A1 | 3/2012 | Hegemann |
| 2012/0077145 A1 | 3/2012 | Tsurukawa et al. |
| 2012/0141952 A1 | 6/2012 | Snyder et al. |
| 2012/0189976 A1* | 7/2012 | McDonough ...... A61C 17/0202 433/89 |
| 2012/0266396 A1 | 10/2012 | Leung |
| 2012/0277677 A1 | 11/2012 | Taylor et al. |
| 2012/0277678 A1 | 11/2012 | Taylor et al. |
| 2012/0295220 A1 | 11/2012 | Thomas et al. |
| 2014/0193774 A1 | 7/2014 | Snyder et al. |
| 2014/0259474 A1 | 9/2014 | Sokol et al. |
| 2014/0352088 A1 | 12/2014 | Wu |
| 2016/0151133 A1 | 6/2016 | Luettgen et al. |

FOREIGN PATENT DOCUMENTS

| | | |
|---|---|---|
| DE | 1466963 | 5/1969 |
| DE | 1566490 | 11/1970 |
| DE | 2409752 | 9/1975 |
| DE | 2545936 | 4/1977 |
| DE | 2714876 | 10/1978 |
| DE | 2910982 | 2/1980 |
| EP | 0023672 | 7/1980 |
| EP | 0515983 | 2/1992 |
| FR | 2556954 | 6/1985 |
| FR | 2654627 | 5/1991 |
| GB | 1182031 | 2/1970 |
| GB | 2018605 | 10/1979 |
| GB | 2237505 | 5/1991 |
| JP | 2-134150 | 4/1990 |
| JP | 2009-39455 | 2/2009 |
| WO | WO95/16404 | 6/1995 |
| WO | WO01/10327 | 2/2001 |
| WO | WO01/19281 | 3/2001 |
| WO | WO2004/021958 | 3/2004 |
| WO | WO2004/039205 | 5/2004 |
| WO | WO2004060259 A2 | 7/2004 |
| WO | WO2008157585 A1 | 12/2008 |
| WO | WO2013/095462 | 6/2013 |
| WO | WO2013/124691 | 8/2013 |
| WO | WO2014145890 | 9/2014 |

OTHER PUBLICATIONS

The Right Tool, Electron Fusion Devices, Inc., 2 pages, at least as early as Feb. 1991.
Japanese Packaging, 2 pages, at least as early as Dec. 2002.
Japanese Instruction Brochure, 20 pages, at least as early as Dec. 2002.
Brochure: Woog International, "You have a 98% chance of getting gum disease. Unless you read this.", Lancaster, Pennsylvania, 5 pages, Feb. 1987.
Brochure: Woog International, "We put the control of home dental care back into the hands of the professional", Lancaster, Pennsylvania, 2 pages, Feb. 1987.
Brochure: WOOG International, "Products at a Glance: Home Dental Care System" WOOG ORAJET, 3 pages, at least as early as Dec. 18, 1998.
Website: http://www.just4teeth.com/product/Panasonic/Panasonic_Portable_Irrigator.htm, 2 pages, at least as early as Jun. 20, 2003.

(56) References Cited

OTHER PUBLICATIONS

Website: http://www.videodirectstore.com/store/merchant.mv?Screen=PROD&Product_Code=EW1'..., 2 pages, at least as early as Jun. 20, 2003.
Website: http://www.products.consumerguide.com/cp/family/review/index.dfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, Jul. 5, 2007.
European Search Report, EPO Application No. 07252693.2, 14 pages, Apr. 28, 2008.
European Examination Report, EPO Application No. 07250799.9, Feb. 5, 2009.
International Search Report, Application No. PCT/US2010/028180, 2 pages, May 18, 2010.
International Search Report, PCT/US2010/060800, 2 pages, Feb. 11, 2011.
International Search Report, PCT/US2011/052795, 10 pages, Jan. 17, 2012.
Waterpik SinuSense Website: http://www.insightsbyapril.com/2012/03/waterpik-natural-remedy-for-sinus.html, 8 pages, retrieved on May 31, 2012.

\* cited by examiner

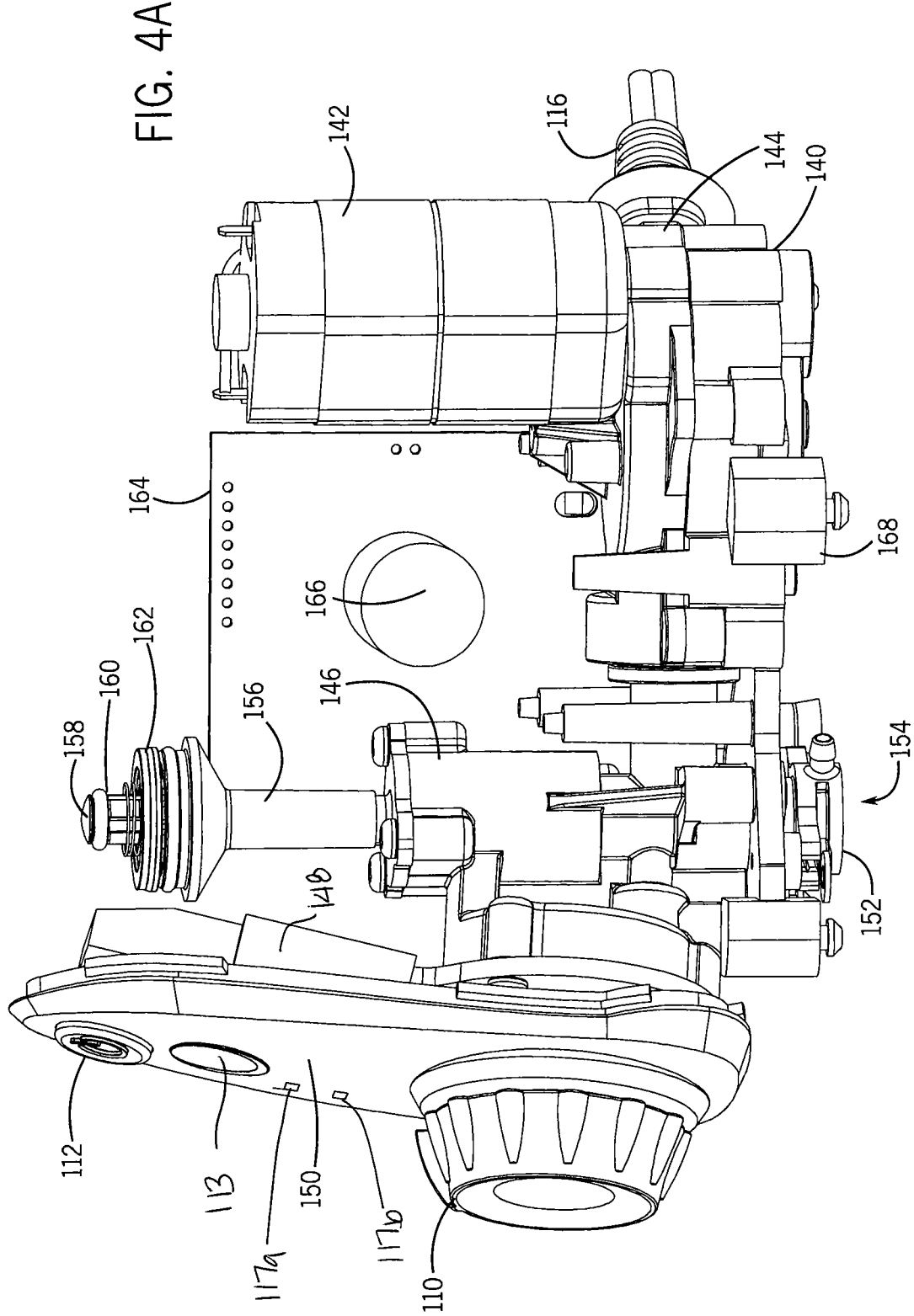

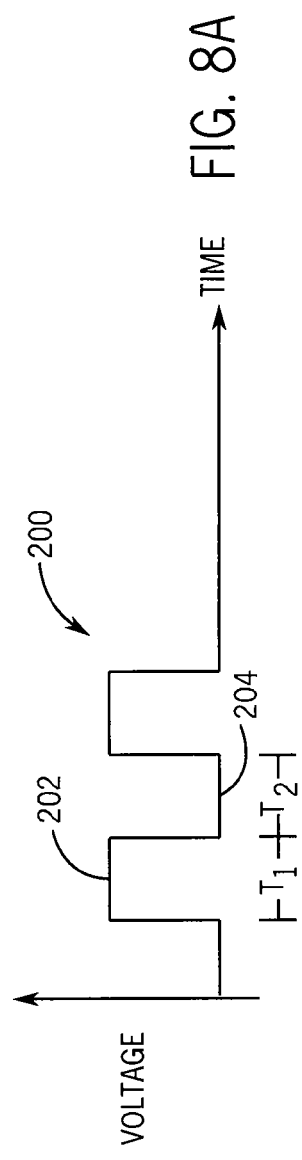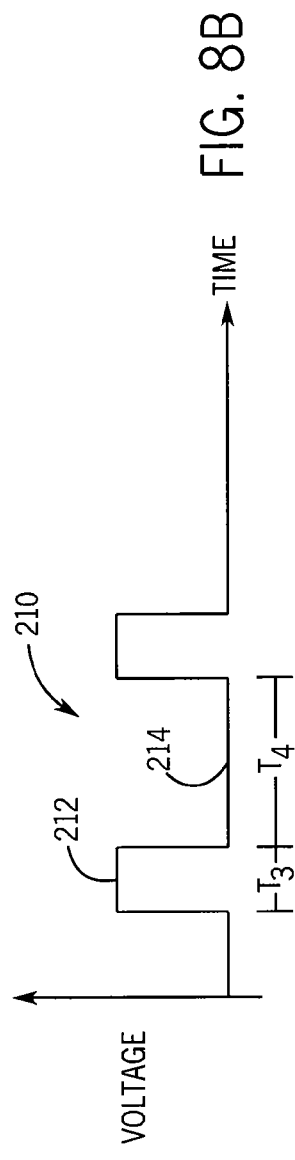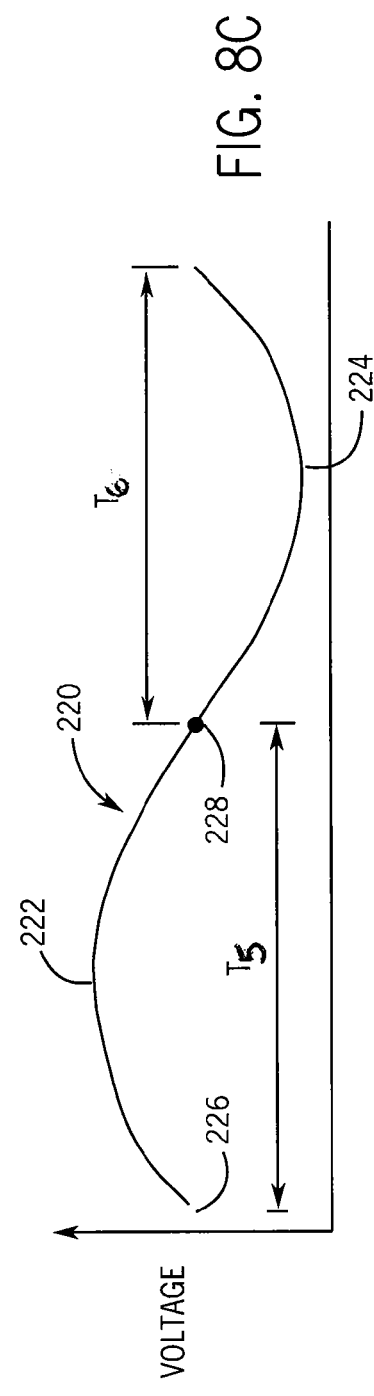

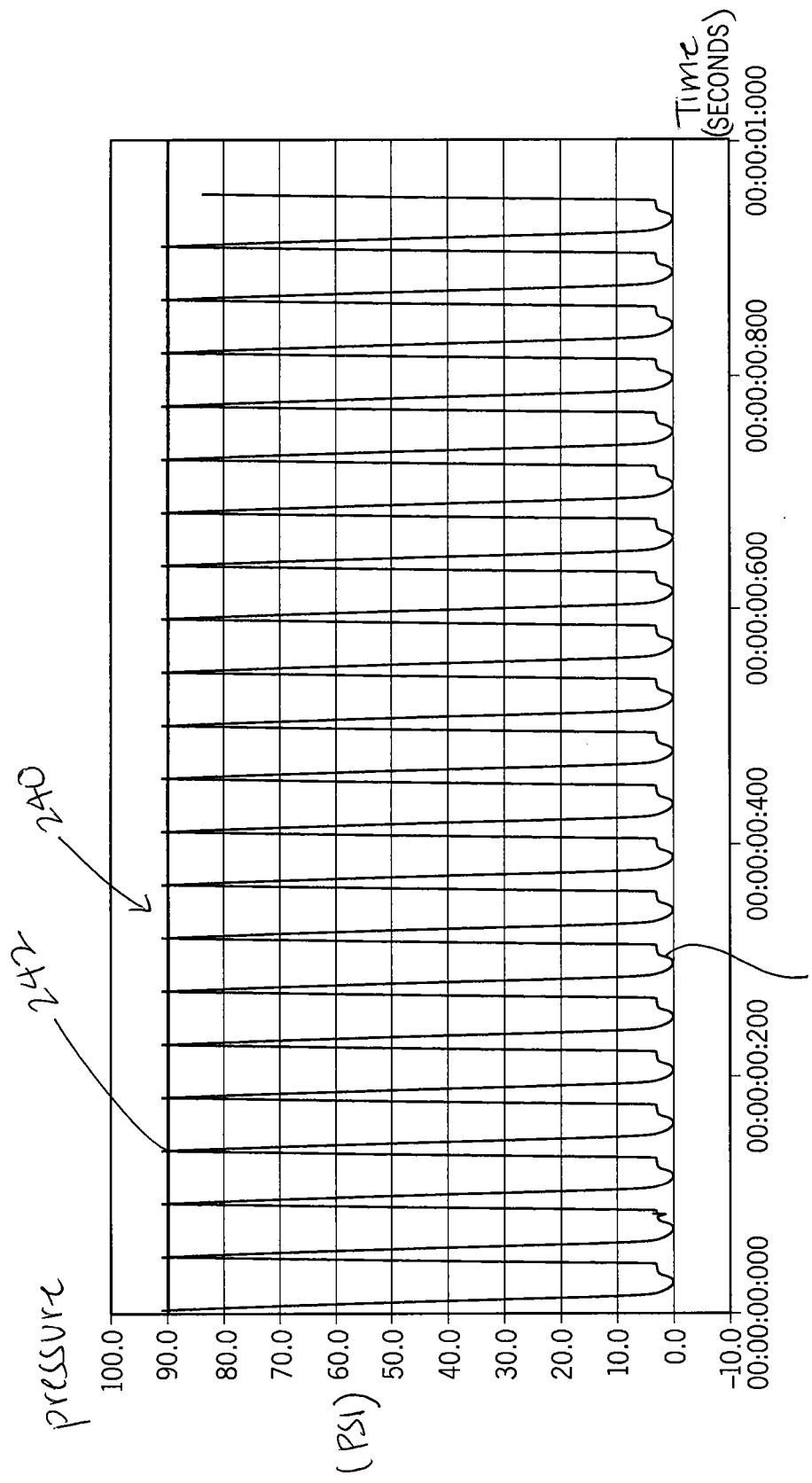

US 9,642,677 B2

ORAL IRRIGATOR WITH MASSAGE MODE

TECHNICAL FIELD

The present invention relates to health and personal hygiene equipment and methods of controlling such equipment. More particularly, the present invention relates to oral irrigators and methods of controlling such equipment.

BACKGROUND

Oral irrigators typically are used to clean a user's teeth and gums by discharging a pressurized fluid stream into a user's oral cavity. The fluid impacts the teeth and gums to remove debris. Often, some users may prefer one pressure level whereas others may prefer another pressure. However, typically, the pressure level may be determined by characteristics of the pump and motor and may not be variable between users. For example, certain flow characteristics, such as pressure, are determined by a mechanical valve, cavity or fluid passage size, or the like, which may not be altered based on particular user preferences and may be complicated to manufacture.

SUMMARY

One example may take the form of a handheld oral irrigator general includes an irrigating device, such as an oral irrigator or a nasal irrigator. The irrigating device includes a pump and a motor connected to the pump and configured to selectively drive the pump. Additionally, the irrigating device includes a massage module in communication with the motor. During a normal mode, the pump has a first pulse rate and during a massage mode, the massage module provides a massage control signal to the motor, causing the pump to have a second pulse rate.

Another example may take the form of a method for varying a pulse rate for an oral cleaning device. The method includes activating a motor connected to pump; determining by a processing element whether a massage mode should be activated; if the massage mode is activated, providing a massage signal to the motor, causing a massage pulse rate output by the pump; and if the massage mode is not activated, providing a normal signal to the motor, causing a normal pulse rate output by the pump.

Yet another example may take the form of an oral irrigator. The oral irrigator includes a reservoir defining a fluid cavity, a pump in fluid communication with the fluid cavity, and a motor connected to the pump and configured to selectively activate the pump. The oral irrigator may also include a handle in fluid communication with the pump and a signal generator in communication with the motor and configured to selectively vary a control signal provided to the motor to vary one or more output characteristics of the motor.

While multiple examples are disclosed, still other examples of the present invention will become apparent to those skilled in the art from the following detailed description, which shows and describes illustrative examples of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 4A is a front perspective view of the oral irrigator with select components hidden for clarity.

FIG. 8A is diagram of a first control signal produced by the massage module.

FIG. 8B is a diagram of a second control signal produced by the massage module.

FIG. 8C is a diagram of a third control signal produced by the massage module.

FIG. 9A is a chart illustrating an example of pressure ranges for the oral irrigator during clean mode.

DETAILED DESCRIPTION OF THE INVENTION

Figure 1A:
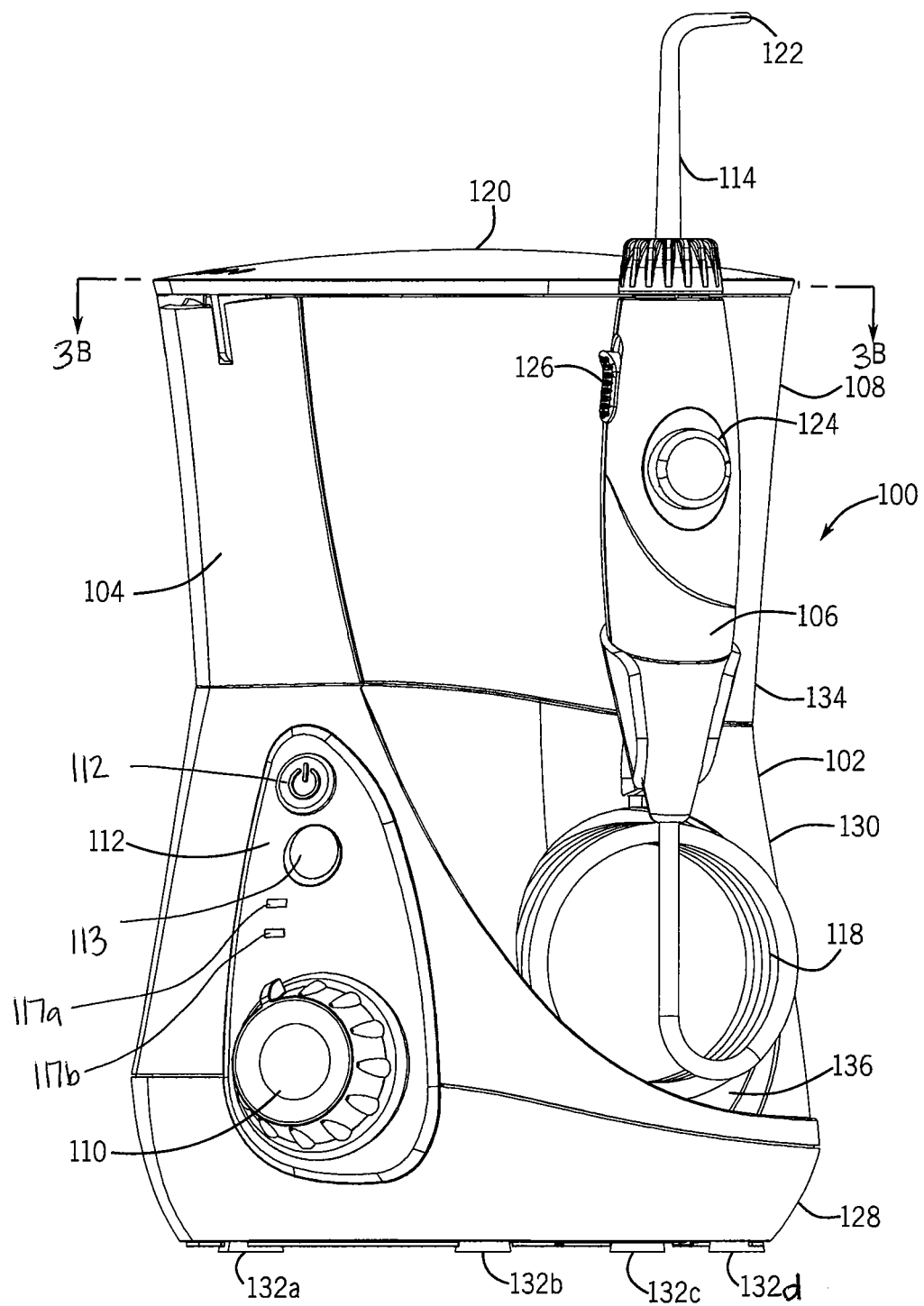
FIG. 1A is a front perspective view of an oral irrigator including a massage module.

Some examples of the present disclosure include an irrigating device, such as an oral irrigator, having a massage module. The massage module may be configured to vary one or more characteristics of a fluid stream to create a fluid flow that may massage a user's gums, as well as enhance user's comfort as the user cleans his or her teeth or gums. The oral irrigator may include a motor and a pump connected to and controlled by the motor. The pump is fluidly connected to a fluid supply and pumps fluid from the supply to an outlet (such as a tip). The massage module may also be in communication with the motor and may provide one or more control signals to the motor to vary one or more characteristics of the motor, such as speed, power, or torque. Because the motor is connected to the pump, as the massage module varies the speed or other characteristic of the motor, the output characteristics of the pump may be correspondingly varied. The output characteristics of the pump may be varied based on a fluid flow that may "massage" a user's gums, such as a pulsed output where the fluid pulses (the flow intermittently turns on an off). In another example, the massage module may vary the outlet fluid pressure of the oral irrigator during massage mode, e.g., may reduce the outlet pressure as compared to clean mode. In this example, the fluid pulse rate may remain substantially the same in both clean mode and massage mode or may also be varied along with the pressure.

In some examples, the oral irrigator may include a cleaning or normal mode and a massage mode. During the cleaning mode, the oral irrigator may include a relatively steady fluid flow or may include a fluid flow having a slight pulse (e.g., due to a mechanical characteristics of the pump). During the massage mode, the massage module may vary the fluid pulsing length and/or pressure. For example, the massage module may vary a control signal to selectively vary the power level provided the motor. In a specific implementation, the power may be selectively activated and deactivated, which may cause the motor to produce intermittent motion resulting in varying the output of the pump. The pump may be selectively activated to create a pulsating fluid flow through the oral irrigator outlet (e.g., the tip).

In one example, the pulses created by the massage module may be longer fluid pulse or breaks in the fluid stream as compared to the normal operation. The increase in pulse length causes the fluid stream to massage a user's gums, enhancing blood flow and providing an enjoyable experience to the user. This is because the pulses may be timed with recovery the gum tissues (e.g., timed to allow blood to flow back into the tissue between each fluid pulse), and provides therapeutic benefits to the gums.

The massage mode may vary one or more characteristics of the control signal based on user input. For example, the user may select the massage mode and may then vary the frequency, magnitude, or shape of the control signal, such as changing the shape of a voltage waveform or its frequency. In other examples, the massage mode may apply a predetermined signal to the motor. For example, a control signal may be determined for the massage mode and when the massage mode is activated by the user, the stored signal may be applied. In these examples, the oral irrigator may include a plurality of control signals that may correlate to different massage modes. In yet other examples, the oral irrigator may include stored signals that may be selected by a user for a predetermined pulsing effect, as well as may vary one or more signals to allow the user to dynamically variable the pulsing effect.

In addition to providing a massage mode, the massage module or another processing element of the oral irrigator may vary one or more output characteristics of the oral irrigator to provide feedback to a user. As a first example, the massage mode may be activated automatically one or more times during normal mode to indicate to a user to move to a different tooth or portion of the mount. As a second example, the massage mode may be activated after a predetermined time period in order to alert the user that a cleaning time (which may be set by the user or be preselected) has expired. As a third example, the massage mode may be activated automatically every time period, e.g., every 30 seconds the massage mode may be activated to provide a massaging feel interspersed with cleaning.

In other examples, the massage module may be used with other irrigating devices. For example, the massage mode may be implemented in a nasal irrigator and may vary the fluid flow rate and pressure to massage the user's nasal tissues. In these examples, the pulse rate and control signal may be varied as compared to the oral irrigator, but may still provide a massaging effect.

In yet other examples, the massage module may be used with other oral instruments to provide a massaging effect and/or to enhance cleaning. For example, the massage module may be incorporated into an electrically driven toothbrush. In this example, the massage module may vary the motor speed or power to vary vibrations or bristle movement.

DETAILED DESCRIPTION

Figure 1B:
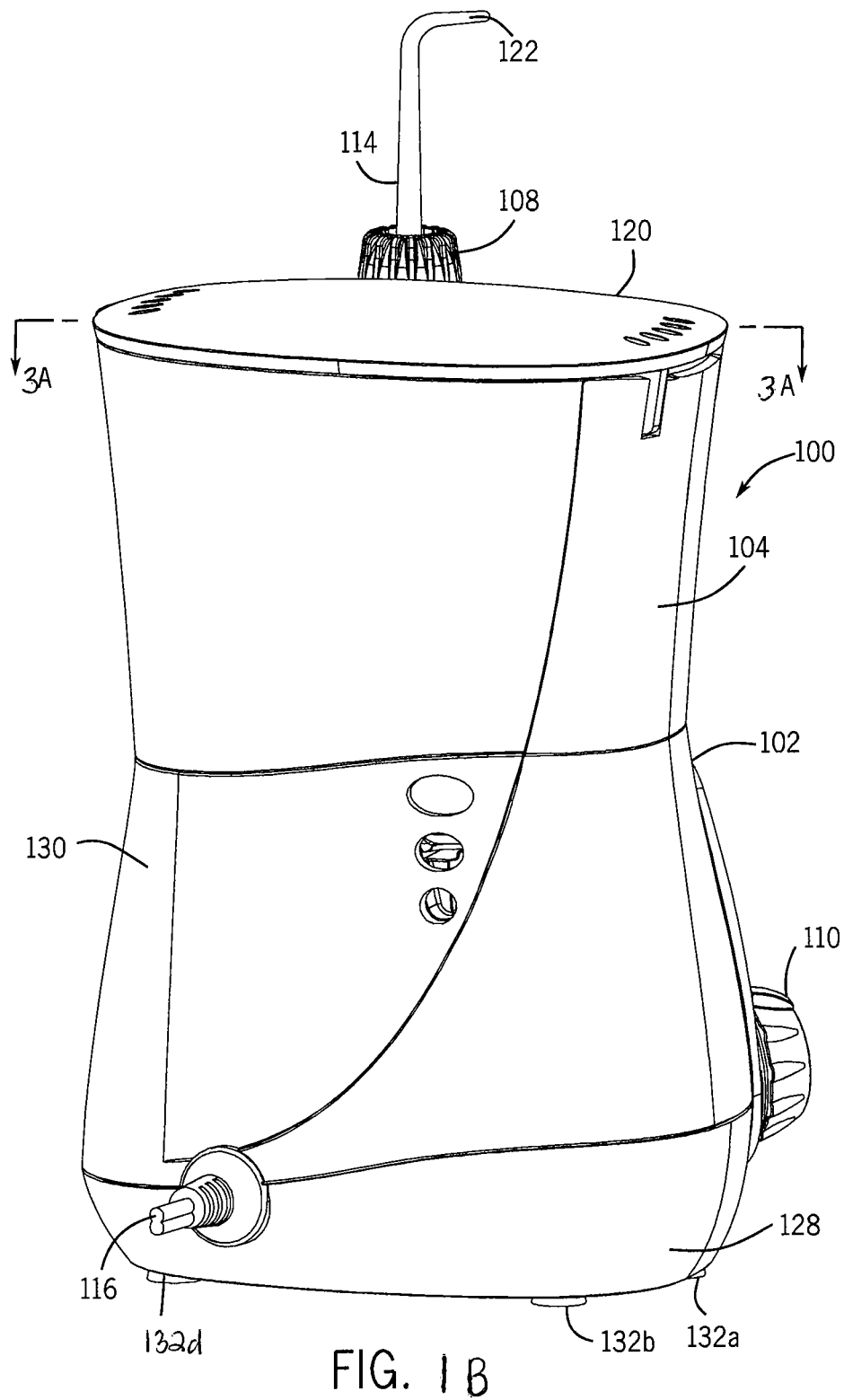
FIG. 1B is a rear perspective view of the oral irrigator of FIG. 1A.
Figure 2:
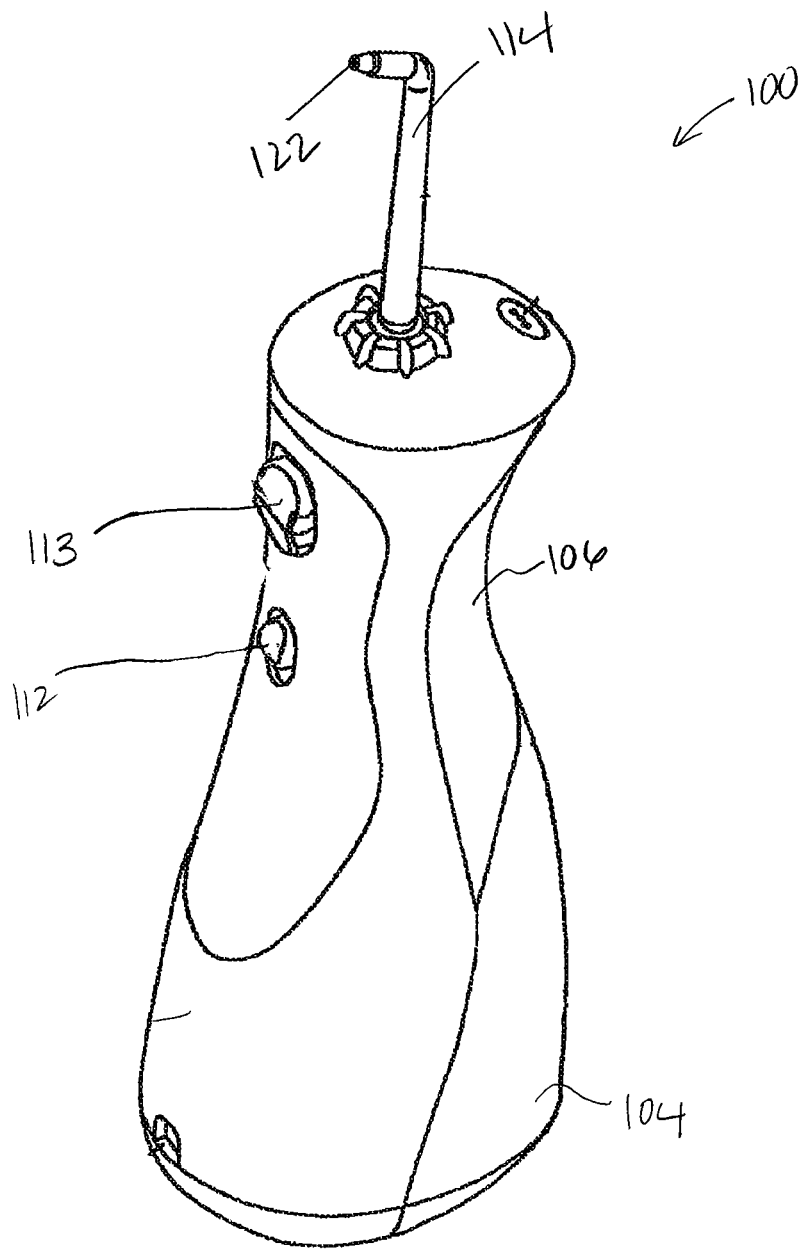
FIG. 2 is a front perspective view of a second example of an oral irrigator including a massage mode.

With reference now to the figures, the oral irrigator will be discussed in more detail. FIG. 1A is a front perspective view of an oral irrigator including a massage mode. FIG. 1B is a FIG. 2 is a rear perspective view of the oral irrigator of FIG. 1A. With reference to FIGS. 1A and 1B, the oral irrigator 100 may include a base 102, a reservoir 104, and a handle 108. The base 102 may provide support for the reservoir 104 and the handle 108, as well as house many of the drive and power assembly components of the oral irrigator 100. For example, the base 102 may house a pump, control circuitry, and/or motor, which will be discussed in more detail below.

The base 102 may include a bottom support 128 and a cover 130. The bottom support 128 may provide support for one or more of the internal components of the oral irrigator 100 and the cover 102 may cover those components to conceal them, as well as provide protection for those components. The base 102 may include a plurality of feet 132a, 132b, 132c, and 132d to support the base 102 on a surface, such as a countertop or the like.

The base 102 may also include a clamp 134 or other structure to releasably support the handle 108. In some examples, the clamp 134 may be a C-clamp; however, other attachment mechanisms are envisioned. The base 102 may also include a hose cavity 136 or hose box that may receive and support the hose 118 in a collapsed position. For example, the hose cavity 136 may include one or more arms on which the hose 118 may be wrapped. The hose cavity 136 may be recessed into the cover 130, may be flush with the cover, or may extend outwards from the cover.

The oral irrigator 100 illustrated in FIGS. 1A and 1B is a countertop irrigator. However, in some examples, the oral irrigator 100 may be a handheld irrigator. FIG. 2 is a front perspective view of a second example of an oral irrigator. With reference to FIG. 2, in examples where the oral irrigator 100 is a handheld unit, the reservoir 104 and handle 106 may be connected together. The reservoir 104 may include a removable cavity that may refilled by a user and then reattached to the handle 106. Additionally, in these examples, the internal components of the irrigator 100, such as the motor, pump, and control circuitry, may be included within the handle 106 rather than a base unit. The description of the oral irrigation described below is generally directed to the oral irrigator illustrated in FIGS. 1A and 1B; however, it should be noted that the description is equally applicable to the oral irrigator 100 shown in FIG. 2, with the exception that the internal components of the base are included in the handle 106.

Figure 3A:
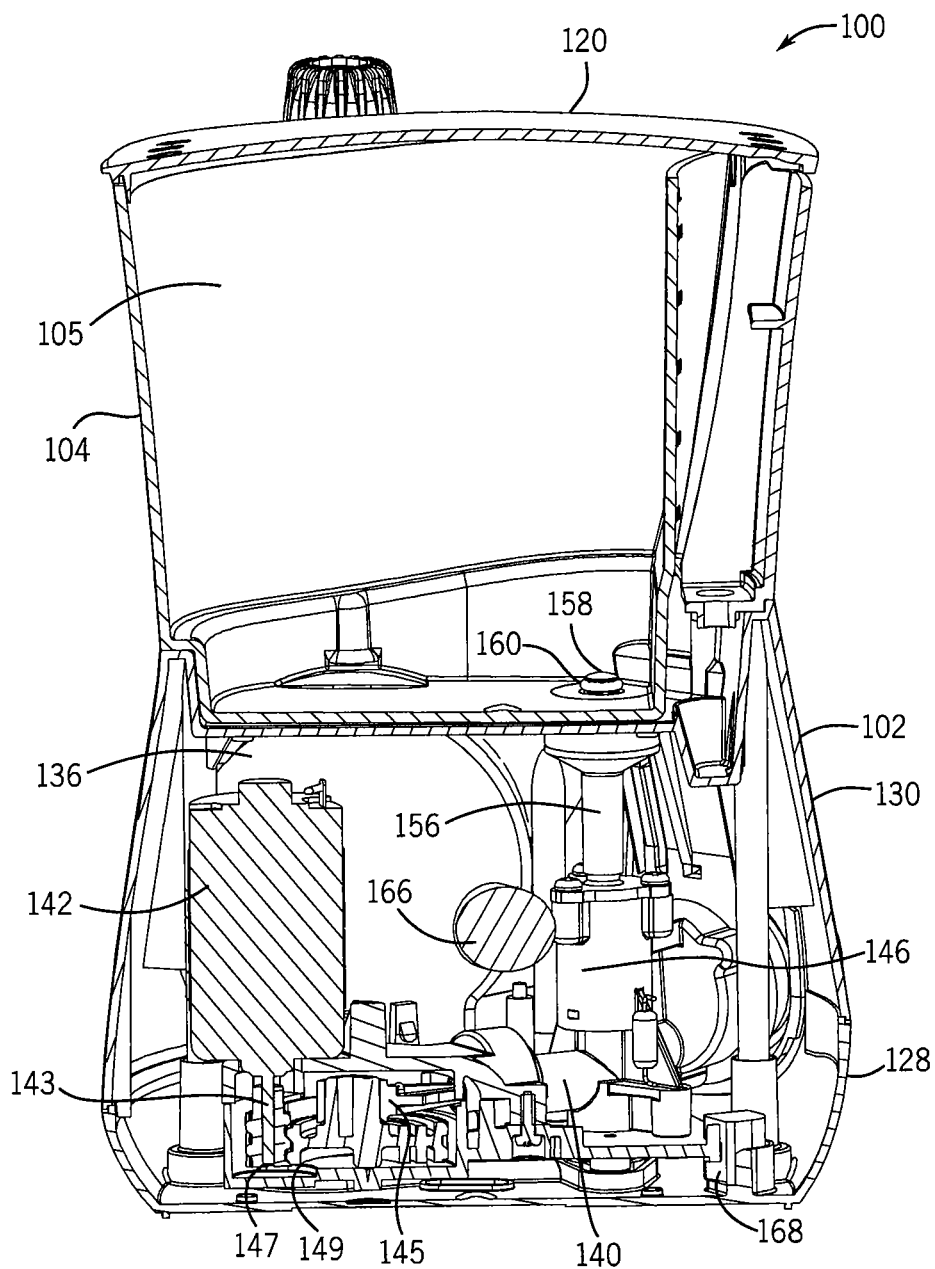
FIG. 3A is a cross-section view of the oral irrigator taken along line 3A-3A in FIG. 1B.
Figure 3B:
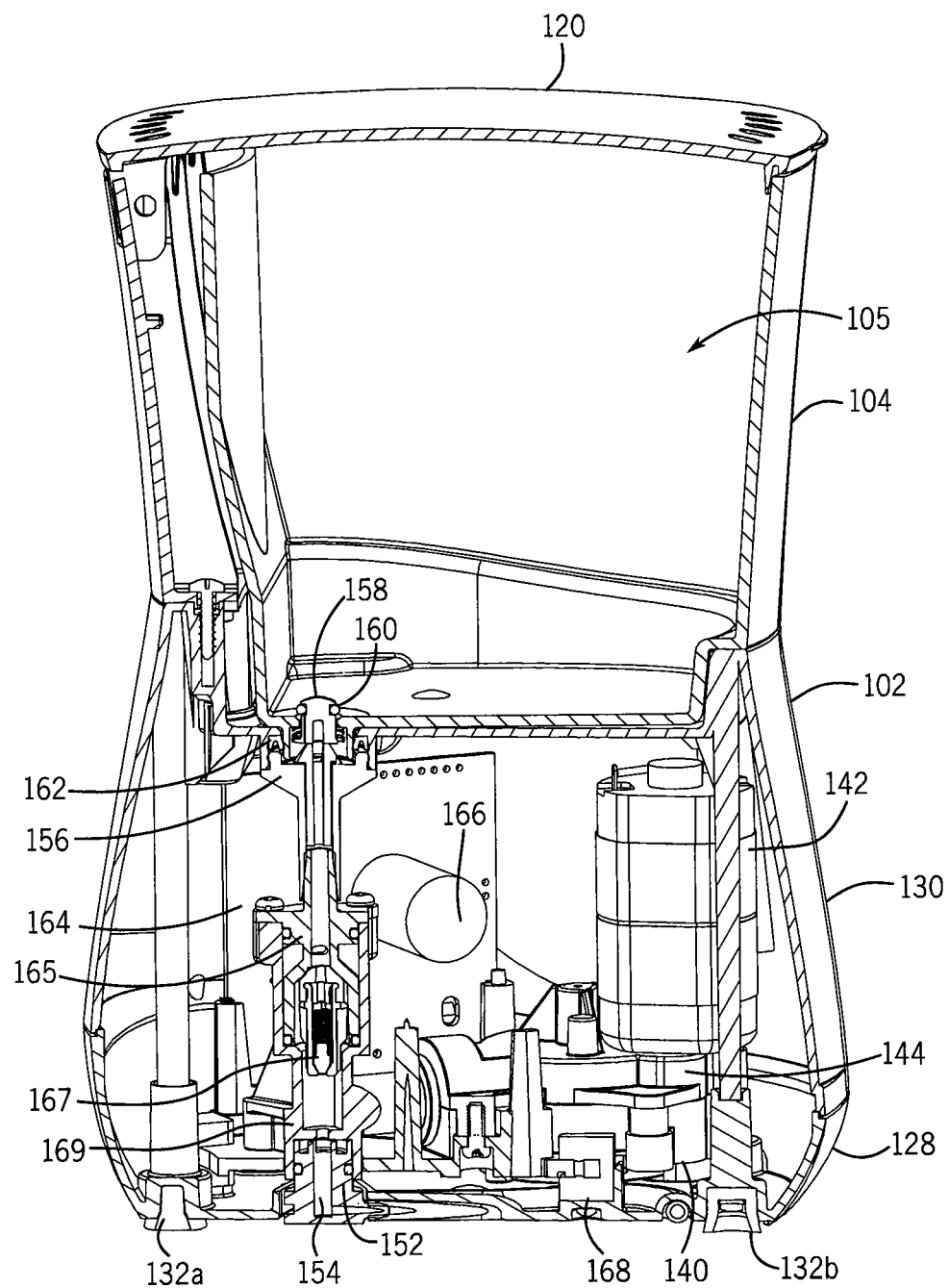
FIG. 3B is a cross-section view of the oral irrigator taken along line 3B-3B in FIG. 1A.
Figure 4B:
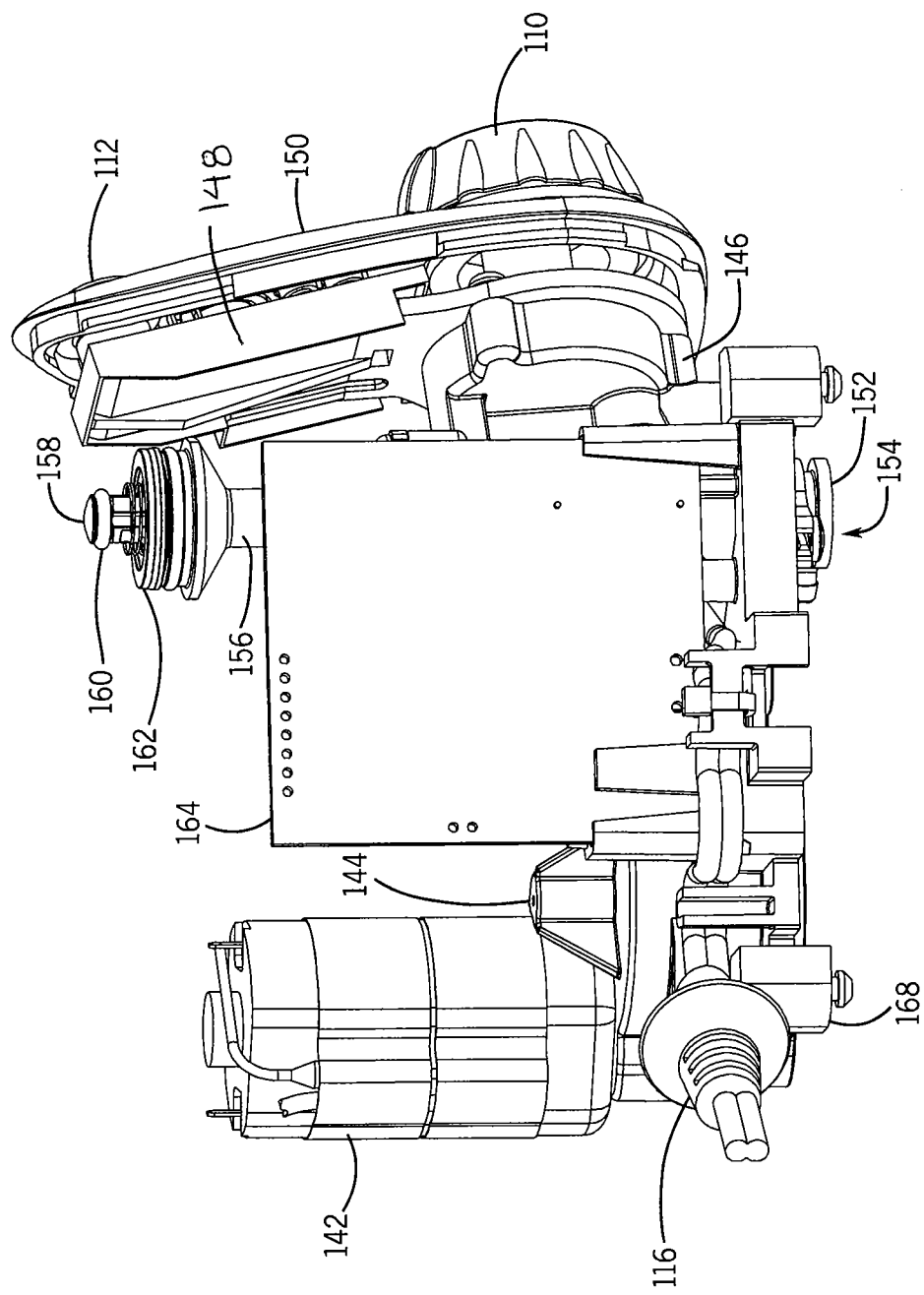
FIG. 4B is a rear perspective view of the oral irrigator with select components hidden for clarity.

FIGS. 3A and 3B are cross-section views of the oral irrigator taken along lines 3A-3A and 3B-3B, respectively, in FIGS. 1A and 1B. With reference to FIGS. 4A and 4B, the reservoir 104 defines a cavity 105 to hold liquid that may be expelled trough a tip 114 connected to the handle 108. The reservoir 104 may include a lid 120 and may be removable from the base 102. In some examples, the oral irrigator 102 may be a handheld or more compact and the reservoir 104 may be incorporated into the handle 108 (e.g., a container attachable to the handle 108). The reservoir 104 may be substantially any size or shape and may be modified as desired, for example, as shown in FIG. 2, the reservoir is included as a cavity attached to the handle.

With reference again to FIGS. 1A and 1B, the handle 108 is movable relative to the base 102 and may be fluidly connected to the reservoir 104. For example, a hose 118 may fluidly connect the reservoir 104 to the handle 108 and tip 114. In examples where the reservoir 104 may be incorporated into the handle 108, the hose 118 may be internal to the handle 108 or may be omitted (e.g., a fluid pathway may be defined through a housing of the handle rather than a tube). In some examples, the handle 108 may include a plurality of internal components, such as a check valves, bypass valves, pause valves, or the like. In these examples, the handle 108 may be used to vary one or more characteristics of the fluid flow output by the tip, separate from or in addition with the features for controlling the fluid output within the base. As mentioned above, although a number of components, such as the pump, reservoir, etc., are discussed herein as being incorporated into the base, in certain examples these components may be included with the handle. For example, as shown in FIG. 2, a handheld oral irrigator may include a portable reservoir attached to the handle with a pump internal the handle. Accordingly, the discussion of any particular example for the handle and base is meant as illustrative only.

The tip 114 may be selectively removable from the handle 108. For example, an eject 126 button can selectively release the tip 144 from the handle 108. The tip 114 defines a fluid pathway that is fluidly connected to the hose 118. The tip 114 includes an outlet 122 from which fluid from the reservoir 104 may be expelled from the oral irrigator 100. The tip 114 may generally be configured to be inserted into a user's mouth and may expel fluid against a user's teeth, gums, tongue, etc. In some examples, the outlet 122 portion of the tip 144 may be shaped as a nozzle or may include a nozzle or other attachment connected thereto.

The oral irrigator 100 may include a plurality of control actuators 110, 112, 113, 124 to control one or more characteristics or parameters of the oral irrigator 100. For example, the control actuators 110, 112, 124 may activate/deactivate the oral irrigator 100, may vary a flow rate, a fluid pressure, a setting (e.g., slow, medium fast), and/or may activate a particular mode, e.g., massage mode. The number of control actuators 110, 112, 113, 124, as well as their structure, size, or shape may be varied as desired. For example, as shown in FIGS. 1A and 1B, the two control actuators 110, 112 on the base 102 are illustrated as rotatable knob or buttons; however, in other examples, the control actuators 110, 112, 113 may be switches, sliders, or the like.

A first control actuator 110 may be configured to vary a fluid pressure of fluid as it exits the tip 114. For example, the control actuator 110 may be connected to a valve that may selectively change the diameter of a fluid outlet or pathway between the reservoir 104 and the tip 114. As the diameter is varies, such as due to a user turning the control actuator 110, the outlet fluid pressure as fluid is expelled from the tip 114 may be selectively modified. As another example, the first control actuator 110 may activate a massage module to activate a massage mode for the oral irrigator 100.

A second control actuator 112 on the base may be configured to selectively power the oral irrigator 100. In other words, the second control actuator 112 may be a power button or knob to turn on the oral irrigator 100. Additionally, in some examples, the second control actuator 112 may activate one or more settings. As an example, the second control actuator 112 may activate and deactivate the oral irrigator 100, as well as select one or more settings, such as a massage mode, low pressure, high pressure, or the like.

A third control actuator 113 on the base may be configured to selectively activate massage mode. In some examples the third control actuator 113 may be positioned adjacent to the second control actuator 112 and may be a compressible button, rather than a knob. However, in other examples, the control actuator 113 may be a knob and may be located on the handle or other portions of the base 102.

In some examples, a fourth control actuator 124 may be disposed on the handle 108. The fourth control actuator 124 may selectively activate one or more settings or may act to pause the oral irrigator 100. By placing the control actuator 124 on the handle 108, the user may more easily change settings or pause the oral irrigator 100 while he or she is using the oral irrigator 100.

The various control actuators 110, 112, 113, 124 may be configured as desired and may change one or more settings or parameters of the oral irrigator 100. For example, any of the buttons 110, 112, 113, 124 may be configured to activate a massage mode for the oral irrigator 100.

The oral irrigator 100 may also include a plurality of lights 117a, 117b, which may be used to provide feedback to a user. For example, the lights 117a, 117b may illuminate, change color, or may pulse to indicate a current mode of the oral irrigator, a pressure level of the oral irrigator, or the like. In a specific example, a first light 117a is illuminated during normal mode and a second light 117b is illuminated during massage mode. See, for example, FIG. 7D.

With reference to FIG. 1B, the oral irrigator 100 may include a power cable 116 or port to receive a power cable. The power cable 116 may be configured to be received into an outlet or power source and may transfer power from a power source to the oral irrigator 100. It should be noted that the type of power cable 116 might be varied based on the power source for the oral irrigator 100. Alternatively, such as the oral irrigator shown in FIG. 2, the oral irrigator 100 may include an integrated power supply; such as one or more batteries, and in these cases the power cord 116 may be omitted or may be used to recharge the integrated power supply (rather than directly provide power to the oral irrigator 100). As will be discussed in more detail below, the power cord 116 may function to act as a power supply for the oral irrigator.

An illustrative example of the internal components of the oral irrigator 100 will now be discussed in further detail. FIGS. 4A and 4B are various perspective views of the oral irrigator 100 with select elements hidden for clarity. With reference to FIGS. 4A-4B the oral irrigator 100 may include a motor 142, a gear box 144, a pump 146, and a chassis 140 supporting the motor 142, gear box 144 and pump 146. A valve assembly 156 including a valve 158 may fluidly connect the reservoir 104 to the pump 146 and a valve fitting 152 may fluidly connect the pump 146 to the hose 118 (and thus the tip 114 and handle 108). Additionally, a check valve 167 may be positioned between the valve assembly 156 and the valve fitting 152. The check valve 167 may regulate fluid pressure of the oral irrigator 100. The oral irrigator 100 may also include a control circuitry 164 having a signal generator 166 in electrical communication with the motor 142.

With reference to FIGS. 3A and 4A, the motor 142 may be substantially any type of motor that may drive movement or create mechanical work sufficient to drive a pump. For example, the motor 142 may be a direct current motor, where the speed of the motor 142 may be controlled by a signal, such as a voltage signal. Control of the motor 142 will be discussed in more detail below.

With reference to FIGS. 3A and 4A, the motor 142 may include a drive shaft 143 (see FIG. 3A) that is connected to a gear shaft 147 and a drive gear 149. The drive gear 149 is connected to a piston 145 or other moveable element within the pump 146. The gear box 144 may cover the gear shaft 147, the drive gear 149, and other mechanical gears or linkage elements that may be used to connect the drive shaft 143 of the motor 144 to the pump 146. The linkage and gear elements may be varied as desired and may depend on the orientation of the motor and the pump relative to one another, the size or speed of the motor, and the like.

The pump 146 may be substantially any type of component that may pump fluid from one location to another. For example, the pump 146 may be a piston driven pump that may selectively push fluid from the reservoir 104 into the hose 118. However, many other pump types are envisioned. Some illustrate pump types include a diaphragm pump or a centrifugal pump. The pump 146 may include a pump body 169 and an inlet pump 165 received within the pump body 169. The first control actuator 110 may be connected to the pump 146 and may be attached to a bypass valve or other control valve (not shown). As discussed briefly above, the first control actuator 110 may selectively vary the pressure of fluid output from the pump 146 and may do so by varying the diameter of a fluid channel between the pump 146 and the tip 114.

With continued reference to FIGS. 3A-4B, the valve assembly 156 may be connected to the pump 146 and received into a bottom of the reservoir. The valve assembly 156 may include a valve 158 and one or more sealing members 160, 162, such as O-rings or sealing cups. The valve 158 may regulate fluid flow from the reservoir 104 into the pump 146. Accordingly, the valve 158 is in fluid communication with the reservoir 104 and provides fluid from the reservoir 104 into the pump 146.

The valve fitting 152 includes a fluid outlet 154 and fluidly connects the pump 146 to hose 118. The valve fitting 152 may be connected to the hose 118 and provide a fluid pathway from the reservoir 104 to the handle 108.

The oral irrigator 100 may also include one or more isolators 168. The isolators 168 may connect the chassis 140 to the bottom support 128 of the base 102. In some examples, the isolators 168 may absorb vibrations from the motor 142 and the pump 146, to reduce the vibrations that may be transmitted to the bottom support 128 and/or feet 132a, 132b, 132c, 132d. For example, the isolators 168 may be an elastomeric material or other material configured to absorb vibrations.

Additionally, in some examples, the oral irrigator 100 may include one or more feedback components. For example, the lights 117a, 117b, which may be light emitting diodes (LEDs) can be used to provide feedback to the user. Continuing with this example, the lights 117a, 117b may be illuminated to indicate the mode of the oral irrigator (e.g., massage mode or normal mode), or may be illuminated to indicate a cleaning or activation time, or the like.

Figure 5:
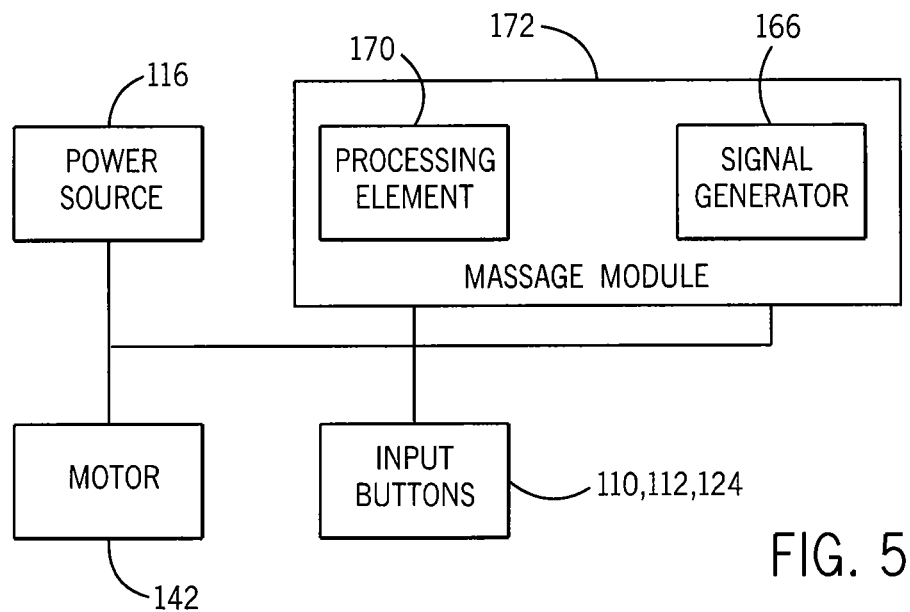
FIG. 5 is a simplified block diagram of the electrical components of the oral irrigator.

The control circuit 164 may control the motor 142 and other elements of the oral irrigator 100. FIG. 5 is a simplified block diagram of the oral irrigator 100 illustrating the electrical communication between select components. With reference to FIGS. 3A and 5, a power source 115 (which may be an outlet in communication via the power cable 116 or one or more batteries) may be in communication with a massage module 172, the motor 142, and optionally, one or more of the input buttons 110, 112, 124. For example, the second control actuator 112 may be in communication with a switch 148 module that may be in communication with control circuitry 164 and/or power source 115 to selectively activate the motor 142.

In some examples, the control circuitry 164 may provide a substrate that supports one or more components, as well as provides communication between those components. For example, the control circuit 164 may be a printed circuit board including one or more traces or connective lines that transmit signals between the massage module 172, the motor 142, and/or the power source 115.

The massage module 172 may selectively control the motor 142 to vary one or more parameters of oral irrigator 100. The massage module 172 may include a signal generator 166 as well as one or more processing elements 170. The processing element 170 may be one or more processors or control chips that may process and execute instructions. The signal generator 166 may be substantially any type of component that may create voltage signals to control one or more characteristics of the motor 142. For example, the signal generator 166 may create one or more repeating or non-repeating electronic signals (e.g., voltage waveforms) that may be applied to the motor 142. In a particular implementation, the signal generator 166 may be a function generator that may produce electrical waveforms over a range of frequencies. Exemplary waveforms include sinusoidal waves, square waves, sawtooth waves, triangular waves, and so on. Additionally, the signal generator may be configured to create modified waves that include characteristics of two or more waveforms. Illustrative waveforms that may be used will be discussed in more detail below with respect to FIGS. 8A-8C.

Figure 6:
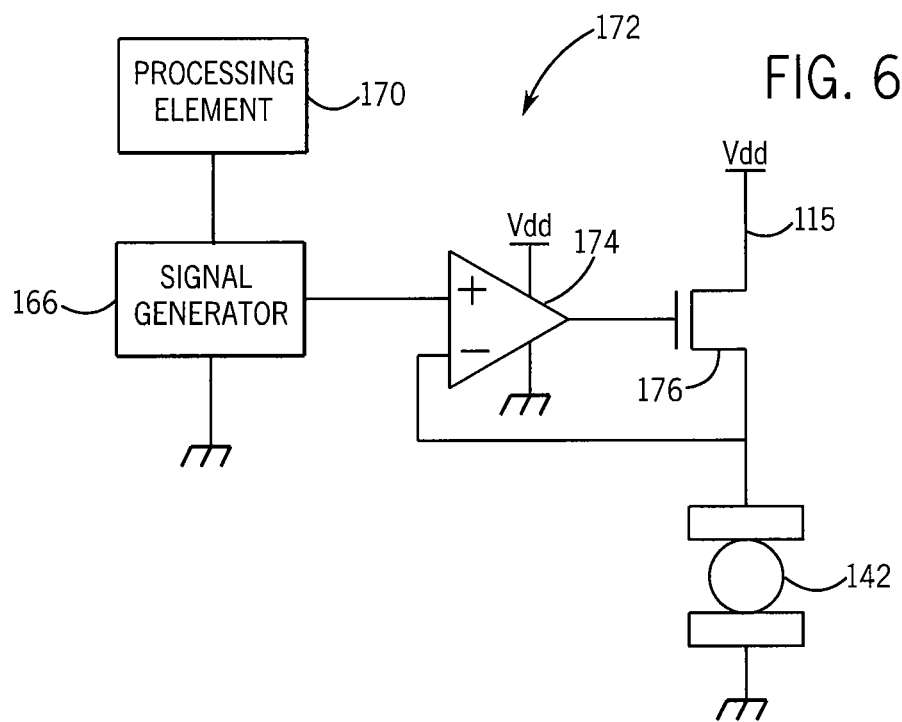
FIG. 6 is a simplified circuit diagram of the massage module.

FIG. 6 is a simplified circuit diagram of the massage module 172. With reference to FIGS. 5 and 6, the signal generator 166 may be in communication with an amplifier 174 and a gate 176 or switch. The signal generator 166 may be in communication with the processor element 170, which may determine the signals generated by the signal generator 166. In some examples, the signal generator 166 may be incorporated into the processing element 170, such that the processing element 170 may perform the functions of the signal generator 166 and may create and apply signals to the motor.

The signal generator 166 may be in communication with an amplifier 174. The amplifier 174 may amplify a signal generated by the signal generator 166 prior to applying the signal to the motor. For example, the amplifier 174 may be an operational amplifier or a differential amplifier. The amplifier 174 may be in communication with the motor 142 as well as the signal generator 166. In some examples, the amplifier 174 may be configured to receive feedback from its output, in order to provide a more consistent output signal. However, it should be noted that the configuration of the amplifier 174, as well as the type of amplifier and inputs used may be varied based on the type of motor 142 and signal generator used 166. Additionally, depending on the output voltage of the signal generator and/or other system characteristics, the amplifier 174 may be omitted. In these instances, the signal may be directly or indirectly applied to the motor without being amplified.

The amplifier 174 may be in communication with a gate 176 or switch. The gate 176 may selectively provide the output of the amplifier 174 (which may be a signal produced by the signal generator 166) to the motor 142. For example, when the gate is not activated, the motor 142 may not receive a signal from the signal generator, but may receive a constant power signal. As another example, when the gate is not activated, the motor 142 may be separated from any signal or power source, preventing the motor from being activated. In this example, the gate 176 provides power to the motor and the signal produced by the signal generator varies the signal transmitted through the gate and during normal mode the motor receives a constant voltage signal and during massage mode the motor receives a variable signal. As yet another example, the activation voltage for the gate 176 may be varied to control the current transmission to the motor. In particular, the gate 176 may be turned slightly activated during one mode allowing a reduced amount of current to travel between its source and drain (when the gate is a transistor) and then may be fully activated to allow full current flow. The variation in current may be used to pulse the signal to the motor or may be used to slow the motor down.

The gate 176 may be a switch or other selectively activated component. In one example, the gate 176 may be a transistor, such as a metal-oxide-semiconductor field-effect transistor (MOSFET), such as an N-channel MOSFET. However, other types of transistors or gates are also envisioned, as well as other components that may be used to selectively provide communication between two or more components.

The massage module and other control circuitry of the oral irrigator may be implemented in a number of different manners, which may vary as desired. FIGS. 7A-7D illustrate various circuit schematics that may be used to implement one or more functions of the oral irrigator, control circuitry, and/or massage module. However, it should be noted that the electrical components, such as resistors, capacitors, and/or gates illustrated may be otherwise configured, omitted, or varied based on a number of a different factors. As such, the schematics illustrated in FIGS. 7A-7D are meant as illustrative and not limiting.

Figure 7A:
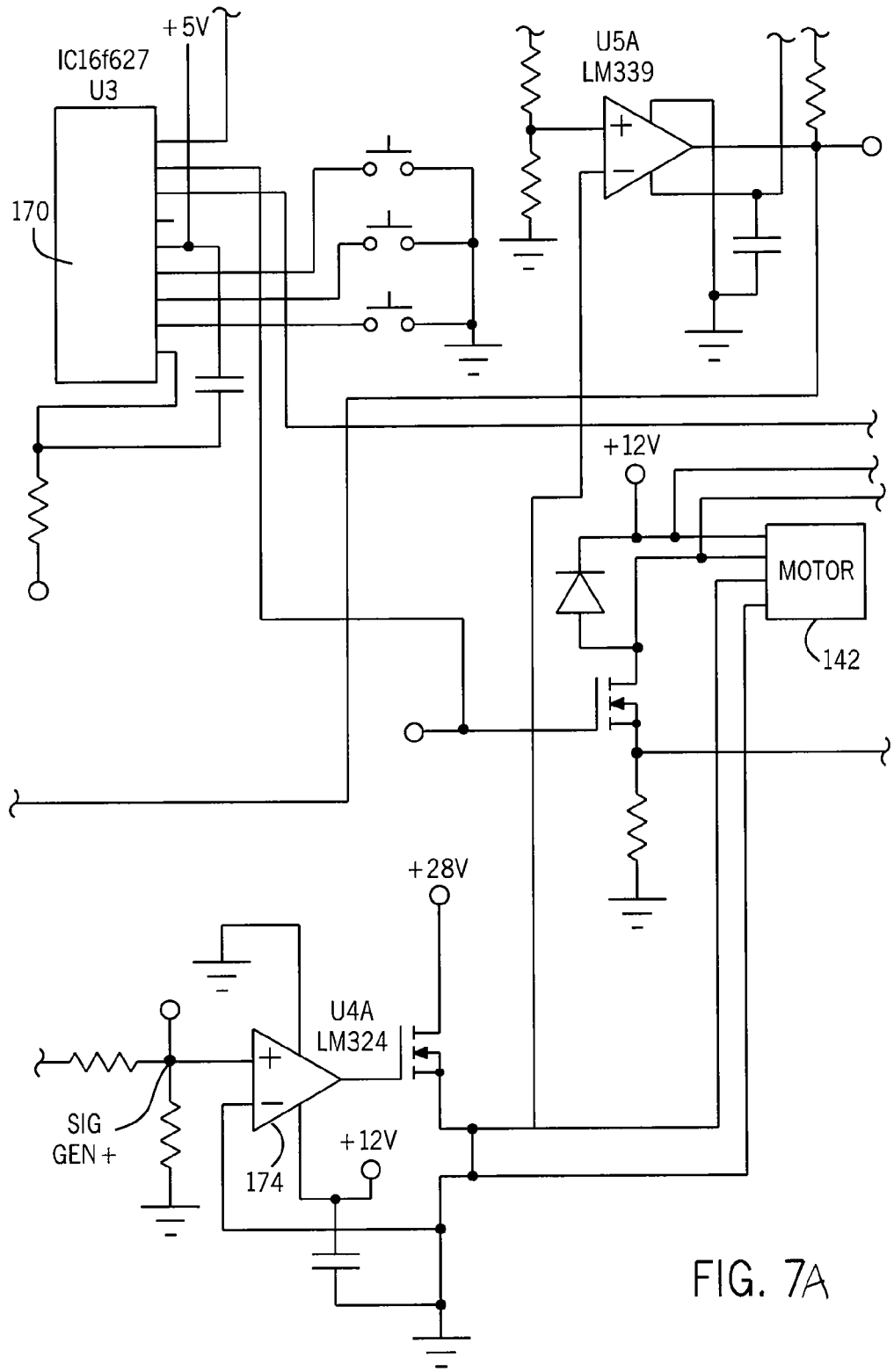
FIG. 7A is a first example of an illustrative circuit schematic for an implementation of the electrical components of the oral irrigator.

FIG. 7A is an illustrative circuit schematic of the control circuitry for one example of the oral irrigator. With reference to FIG. 7A, the circuitry 164 may include a number of electrical components, such as traces, resistors, switches or transistors, and amplifier. The schematic illustrated in FIG. 7A is one example only and the exact components and structures for implementing the massage module may be varied as desired and based on the constraints and parameters of the particular oral irrigator or other device incorporating the massage module.

Figure 7B:
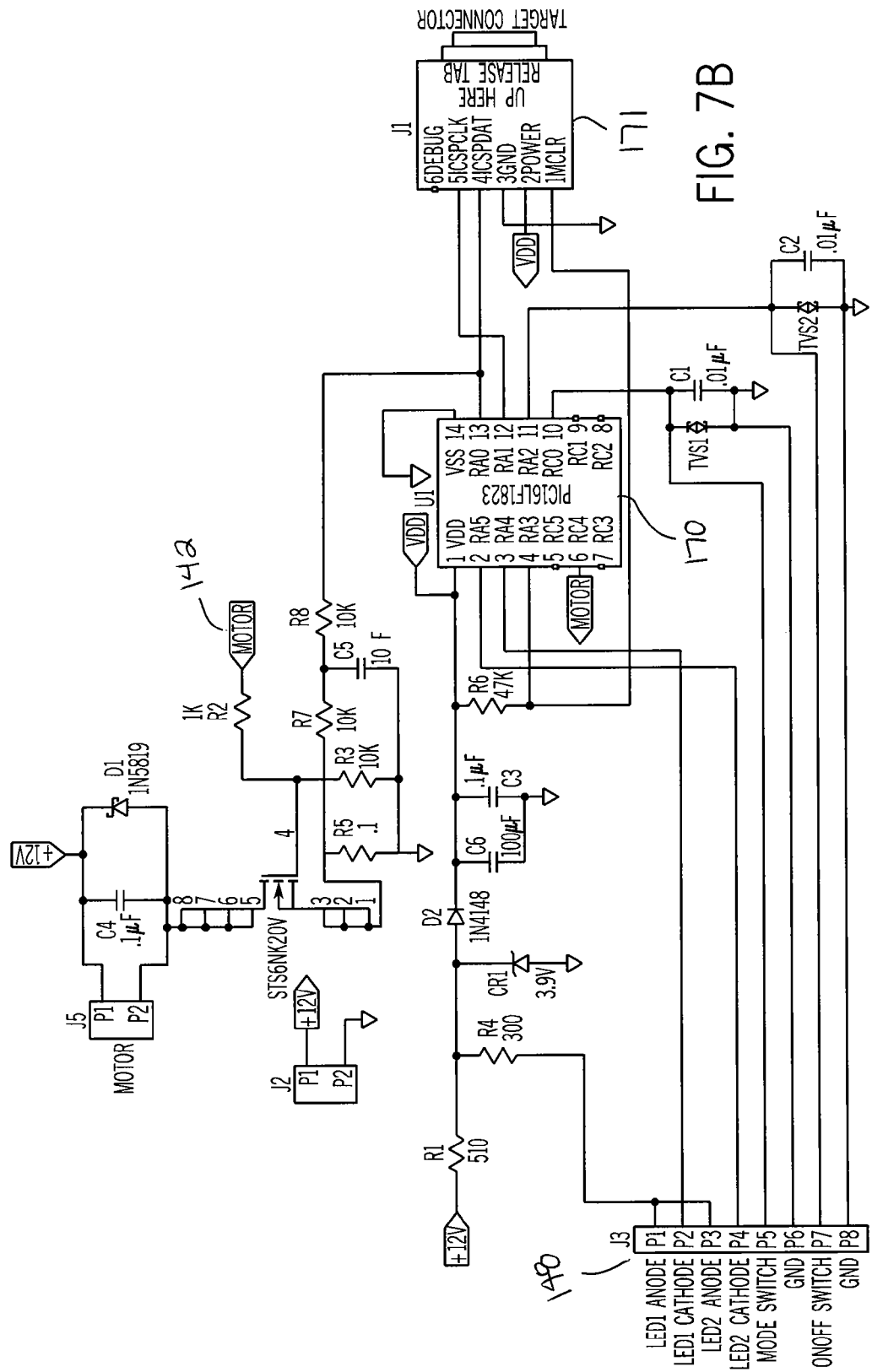
FIG. 7B is a second example of an illustrative circuit schematic for an implementation of the electrical components of the oral irrigator.

FIG. 7B illustrates a second example of a schematic for the oral irrigator. In the example shown in FIG. 7B, the voltage source may be 12V and the processing element 170 and the switch 148 may control operation of the oral irrigator 100. The schematic may also include a second control element 171 that may control a clock signal, data, a reset function, and the like for the oral irrigator. The second control element 171 may be in electrical communication with the processing element 170.

Figure 7C:
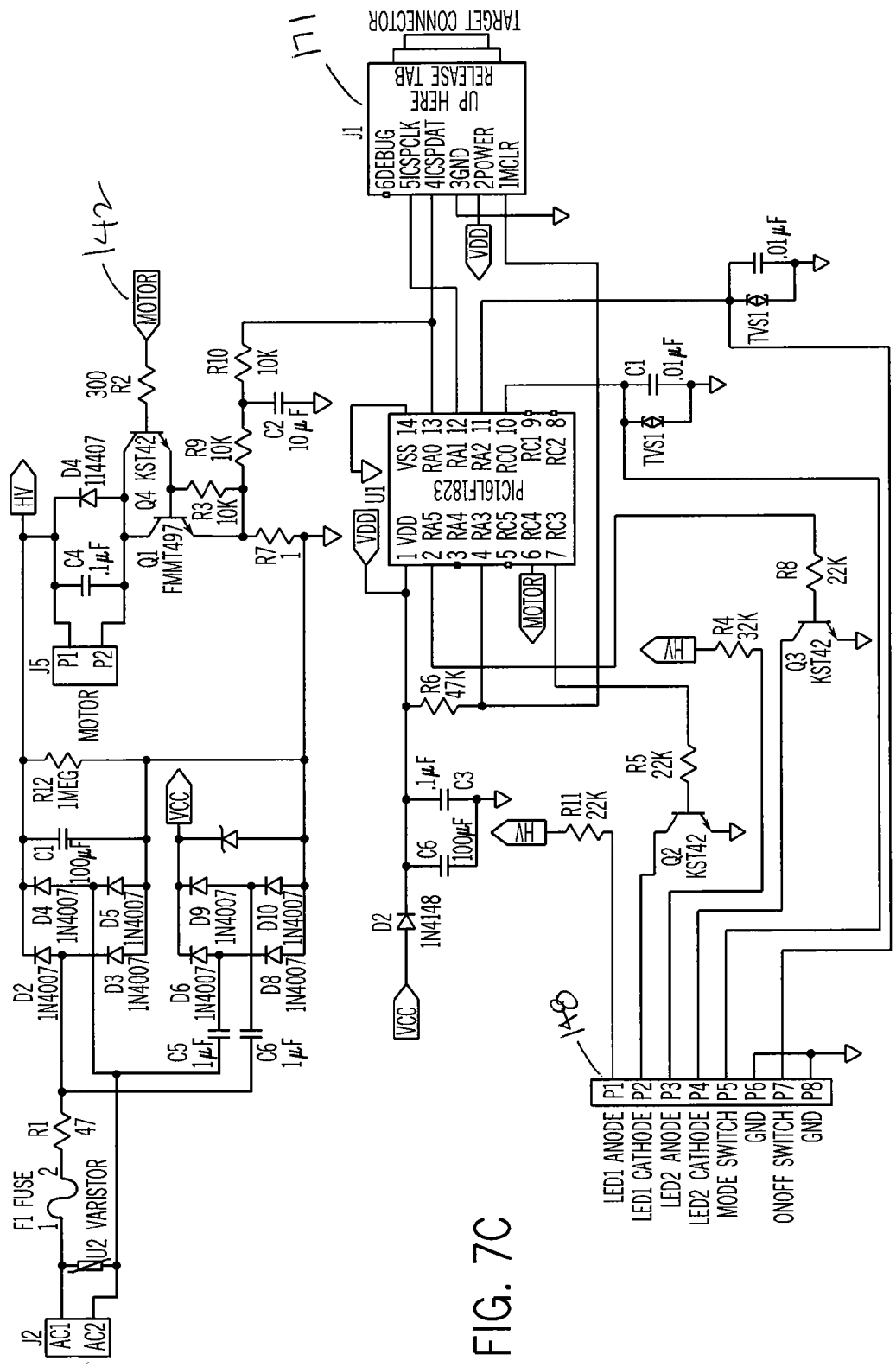
FIG. 7C is a third example of an illustrative circuit schematic for an implementation of the electrical components of the oral irrigator.

FIG. 7C illustrates a third example of a schematic for the oral irrigator. In the example shown in FIG. 7C, the voltage source may be higher than the example shown in FIG. 7B and may include a fuse 181 to help regulate spikes in current and/or voltage. As shown in FIG. 7B, the second control element 171 may also be used to provide clock signals and resets for the oral irrigator 100 and the switch 148 may provide communication between one or more of the control actuators 110, 112, 113, 124 with the processing element 170.

Figure 7D:
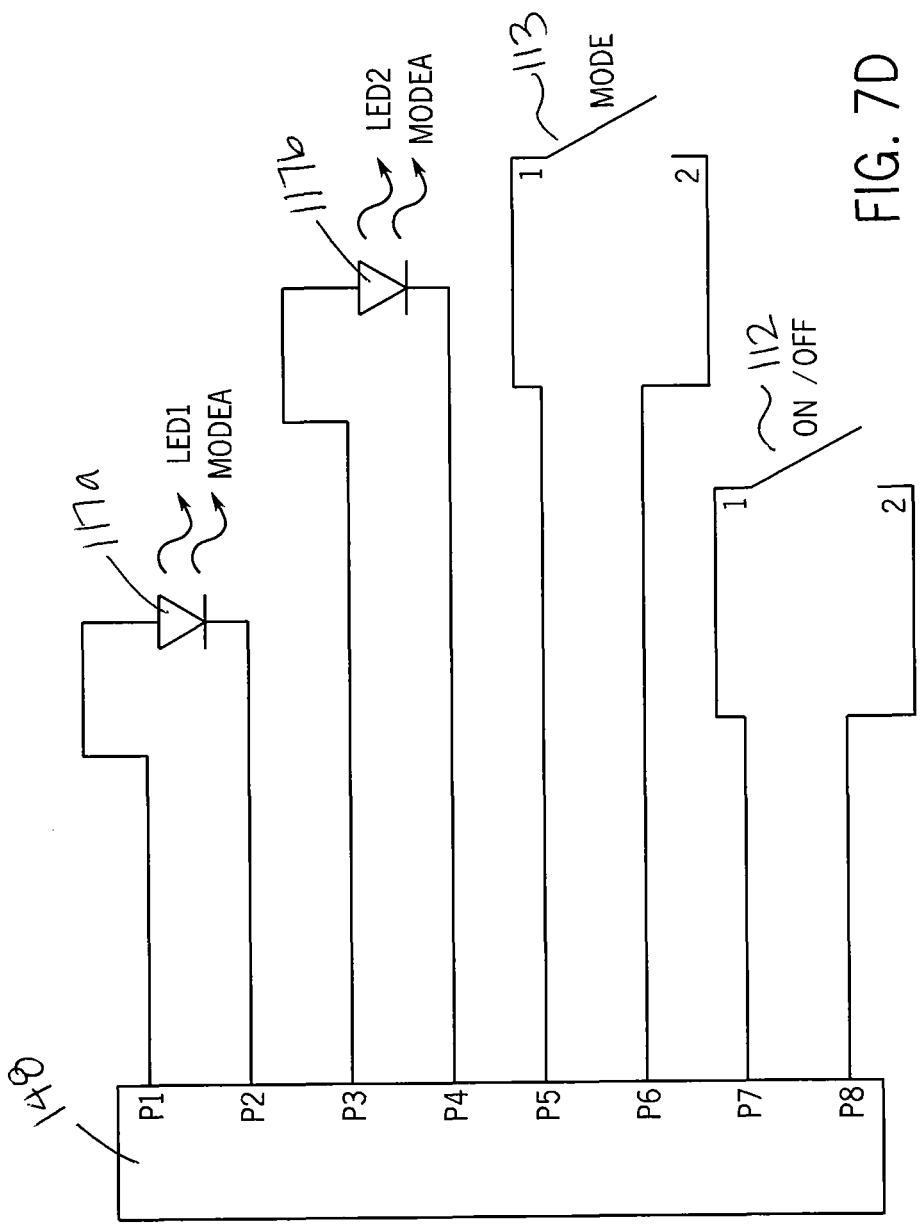
FIG. 7D is an example of a switch control board for the oral irrigator.

FIG. 7D illustrates a diagram of the switch 148 and light module. With reference to FIGS. 7B, 7C, and 7D, the switch 148 module may be in communication with the processing element 170, the lights 117a, 117b, the second control actuator 112, and the third control actuator 113. With reference to FIG. 7D, when the second control actuator 112 is activated by the user, the switch 148 may provide a signal to the processing element 170, which may activate the oral irrigator 100. Additionally, the switch 148 may activate the first light 117a to indicate that the oral irrigator 100 has been activated and is in the normal mode. For example, the normal or clean mode may be a default mode that may be activated when the oral irrigator 100 is initially activated.

With continued reference to FIGS. 7B, 7C and 7D, when the second control actuator 113 is activated by the user, the switch 148 may provide a signal to the processing element 170 indicating that the user has activate the massage mode or second mode. Additionally, the switch 148 may illuminate the second light 117b to indicate to the user that the massage mode has been activated. In the example shown in FIG. 7D, both lights 117a, 117b may be light emitting diodes. However, in other embodiments, other light sources are envisioned.

With reference again to FIGS. 1A-6, in operation, the user may rotate, push, or otherwise provide an input to the second control actuator 112. The second control actuator 112 may activate the oral irrigator 100, causing the power supply 115 to provide power to the control circuitry 164 and the motor 142. During normal operation, control circuitry 164 will provide a normal control signal to the motor 142. For example, the voltage or power source 115 may be placed into communication with the motor 142 and may provide a substantially constant control signal to the motor 142. As the motor 142 receives the constant control signal, the motor 142 may begin turning the drive shaft 143, moving the piston 145. As the piston moves, fluid from the reservoir 104 may be pulled through the valve 158 into the pump 146 and be pushed through the outlet 154 of the valve fitting 152 into the hose 118. The fluid may then travel through the hose 118 to the handle 108 and exit out of the tip 114.

During normal operation, the control signal to the motor 142 may be substantially constant, causing the motor 142 to rotate the drive shaft in a constant manner (e.g., having a constant velocity). In examples where a piston pump or other reciprocating pump is used, the fluid may be slightly pulsed as it is expelled from the tip 114. This is due to the reciprocating nature of the pump, e.g., the alternating pulling and pushing to alternately pull fluid from the reservoir 104 and push fluid from the pump out to the tip 114. Depending on the type, size, or the like, the pulses during normal operation may have a somewhat short duration and fast frequency. In one example, the pulses due to the reciprocating nature of the pump 146 may be about 26 pulses per second. However, in other examples, during normal mode, the fluid outlet may not be pulsed, but may be substantially constant. For example, in examples where a non-reciprocating pump is used, the output during normal mode may be substantially constant.

During use, if the user hits the pause actuator 124, a valve within the handle 106 may reduce or substantially prevent fluid from exiting the tip 114. Alternatively or additionally, the fourth control actuator 124 may transmit a signal to the processing element 170 that may temporarily stop movement of the motor 142, to prevent or reduce fluid transmitted from the reservoir 104 to the tip 114. Also, if the first control actuator 110 is activated, the user may selectively adjust the pressure of fluid expelled from the tip 114.

If massage mode is activated, such as by a user providing an input to the oral irrigator 100 through one of the control actuators 110, 112, 113, 124, the fluid output characteristics may be modified. For example, the third control actuator 113 may be used to activate a massage mode for the oral irrigator 100. During massage mode, the processing element 170 may selectively activate the gate 176, to vary the signal provided to the motor 142. In one example, the signal generator 166 may apply a varying signal to the motor 142, which may cause the motor 142 to selectively vary one or more movement characteristics. For example, the signal generator 166 may apply a signal that has a variable voltage across a predetermined time duration. The signal may vary not only in voltage magnitude, but also in time between a high voltage and a low voltage (e.g., frequency).

With reference to FIG. 6, the amplifier 174 may increase the signal generated by the signal generator 166 and provide the increased control signal to the motor 174. The control signal may selectively interrupt or vary the power supplied to the motor 142, causing the motor to intermittently stop or slow down, reducing, stopping, or changing the movement of the drive shaft 143. As the drive shaft 143 varies, the piston 145 may also vary, which may increase the length of pulses produced by the pump 146, as well as the pressure output by the pump 146. As an example, when the control signal is low or otherwise prevents power from being transmitted to the motor, the motor 142 may stop rotating the drive shaft 143, which may in turn, stop movement of the piston 145, reducing or stopping fluid from flowing from the reservoir 104 to the tip 114.

Specifically, one control signal may be configured create 0.5 second pulses. In other words, the pump 146 may produce 2 pulses per second, with may have a substantially slower pulse rate than the pulse rate due to the reciprocating nature of the pump, and each pulse may have a substantially longer duration as compared to the normal mode. However, it should be noted that other pulse rates are envisioned and will be discussed in more detail below with respect to FIGS. 8A-8C.

In some implementations, the flow rate of the oral irrigator during massage mode may be reduced as compared to the flow rate during normal mode. As a specific example, the massage mode flow rate may be between 40 to 70 percent and often 50 to 60 percent of the flow rate during normal mode. In some implementations, the oral irrigator 100 may have a flow rate during clean mode ranging between 300-400 mL per minute and often may be about 370 mL per minute and during massage mode the flow rate may range between 150-200 mL per minute or lower and often may be 222 mL per minute.

Figure 9B:
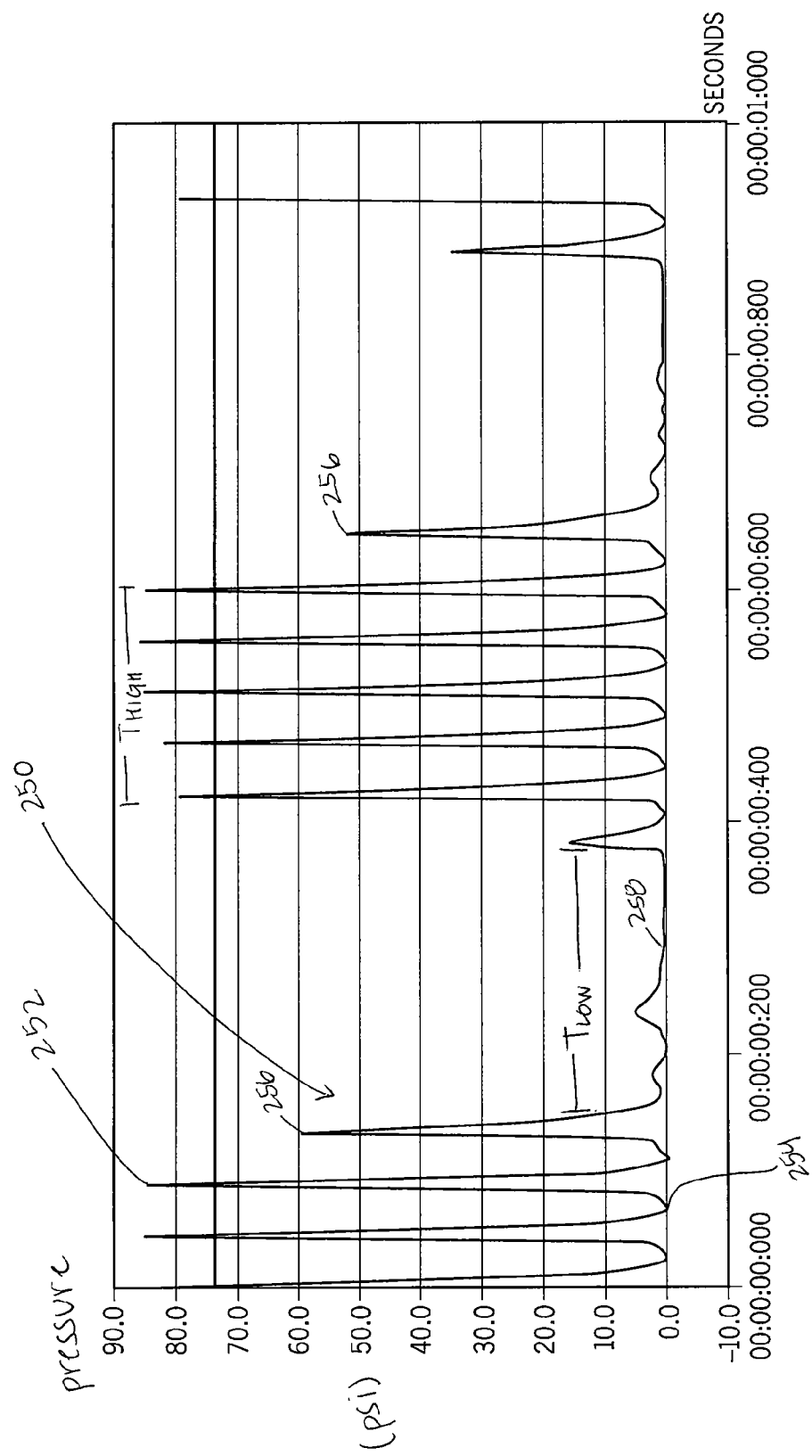
FIG. 9B is a chart illustrating an example of pressure ranges for the oral irrigator during massage mode.

In addition to changing the pulse rate, the control signal may also vary the magnitude of power provided to the motor 142, which may increase or decrease the outlet pressure of the pump 142. In a specific implementation, the outlet pressure of the oral irrigator during cleaning mode may range between 70 to 95 psi, and often average between 90-93 psi and during massage mode may range between 60 to 90 psi, and often average between 80-87 psi. FIGS. 9A and 9B illustrate example pressure ranges for the oral irrigator during normal mode and during massage mode. For example, by applying an increased voltage to the motor 142, the current supplied to the motor 142 may also increase, increasing the torque of the motor 142. The increased torque may exert an increased force on the piston 145, to increase the output pressure of the oral irrigator 100. Accordingly, in some examples, the control signal may vary not only the durations for which a voltage is applied to the motor, but also the magnitude of the voltage in order to vary not only the fluid pulses but also the fluid pressure output by the oral irrigator 100.

As the fluid exits the tip 114, the user may direct the flow on his or her teeth, gums, tongue, cheeks, or the like. The varying control signals may vary the fluid output by the tip 114. In some examples, the variation in fluid may create a massage effect on a user's gums. For example, during each pulse fluid may not exit from the tip 114, allowing blood to return to the user's gums before the next fluid stream hits the gums. This may provide a massaging effect, as well as may stimulate blood flow to the gums and enhance the cleaning experience with the oral irrigator.

The signal generator 166 may vary a frequency and magnitude of the control signal based on a desired output pulse rate and fluid pressure. FIGS. 8A-8C illustrate control signals that may be created by the signal generator to be applied to the motor 142. The control signals may include one or more voltage peaks and voltage minimums. As some illustrative examples, the voltage peaks may be 170V, 12V, 6V, or other values and the voltage minimums may be a subset of the voltage peaks and often may be substantially or about 0V. However, it should be noted that many other voltage values are envisioned and the voltage of the control signal may depend on the motor, the processing element, and other system parameters and as such may be modified as desired.

With reference to FIG. 8A, a control signal 200 may be a square wave having a voltage peak 202 or amplitude and a voltage minimum 204. In some examples, the voltage peak 202 (i.e., maximum voltage) may be applied for a duration T1 and the voltage minimum 204 may be applied for a duration T2. In this example, the durations T1 and T2 may be approximately equal. In a particular implementation, the peak voltage 202 may be approximately 12 V and the minimum voltage 204 may be 0 V, additionally both durations T1 and T2 may have a length of approximately 100 ms.

When the control signal 202 of FIG. 8A is applied to the motor 142, during the duration T2 of the minimum voltage 204, the motor 142 may not receive power. In other words, because the minimum voltage 204 is set to 0 V, the motor 142 may not be powered. As the motor 142 does not receive power during the duration of the minimum voltage 204, the drive shaft 143 may slow down and stop moving, stopping movement of the piston 145 within the pump 146. Thus, during the duration T2, the pump 146 may not pump fluid, creating a pause in fluid flow. Then, when the peak voltage 202 is applied, the motor 142 may begin rotating the drive shaft 143, causing the piston 145 to push fluid from the pump 146, creating fluid flow. In this example, the minimum voltages 204 may define the "pulse" length, or the intermission between fluid output.

With continued reference to FIG. 8A, in another example, the maximum voltage 202 may be selected to be approximately 12V and the minimum voltage 204 may be selected to be approximately 6 V or half of the maximum voltage. However, in other embodiments, the minimum voltage may be 0V in this example as well. Additionally, the two time durations may be selected to be 160 ms. In this example, during second duration T2 when the minimum voltage 204 is applied to the motor 142, the motor 142 may receive some power, but the power may be reduced as compared to the maximum voltage 202. In this example, the motor 142 may still rotate the drive shaft 143, but may do so at a reduced torque and speed, which may also cause a reduced flow rate and pressure output by the pump 146. In this example, during each pulse, fluid may be output from the tip 114, but at a slower flow rate and pressure.

In yet another implementation, the time durations T1 and T2 may be selected to be 250 ms. In these examples, the frequency of the pulses may be reduced, such that there may be fewer pulses per second as compared to examples where the time durations may be shorter.

In FIG. 8A, because the time durations T1 and T2 may be substantially equal, the time of fluid output and fluid pause may be substantially the same. However, in other examples, the time durations for the maximum voltage and the minimum voltage may be varied. With reference to FIG. 8B, a control signal 212 may include a voltage maximum 212 having a duration T3 and a voltage minimum 214 having a duration T4. In this example, the peak time duration T3 may be shorter than the minimum time duration T4, which may result in longer "pauses" in fluid flow or pulses. The time duration T4 may be twice, three times, or more, the length of the peak time duration T3.

As one example, the minimum voltage time duration T4 may be three times as long as the maximum voltage time duration T3. Thus, the pause in fluid flow may last three times as long as the fluid flow segments or pulses. In a specific implementation, the maximum voltage 212 may be 12V and may have time duration T3 of 100 ms, the minimum voltage 214 may be 0V and may have a duration of 300 ms. However, the above values are illustrative only and many other implementations are envisioned. Furthermore, although the control signal 210 in FIG. 8B is illustrated as having a longer low voltage duration T4 than maximum voltage duration T3, in some examples, the maximum voltage time duration T3 may be longer than the minimum voltage time duration T4. In these examples, the pauses or breaks between fluid flow may be reduced as compared to the fluid stream time durations.

In the control signals 200, 210 illustrated in FIGS. 8A and 8B, there may be a rapid transition between the maximum or peak voltage 202, 212 and the minimum voltage 204, 214. For example, both control signals 200, 210 may be square waves that substantially instantaneously transition between minimum and maximum values. However, in other examples, the control signal may gradually transition between a maximum and minimum voltage.

With reference to FIG. 8C, a control signal 220 having a sinusoidal shape is illustrated. The control signal 220 may have a peak voltage 220 and a minimum voltage 224, with the peak voltage 220 having a time duration T5 and the minimum voltage having a time duration T6. However, because the control signal 220 may gradually change between the maximum and minimum levels, the durations T5 and T6 may represent the time between inflection points 226, 228. The inflection points 226, 228 generally may represent half of a cycle or period for the control signal 220. In other words, the sum of the durations T5 and T6 may represent the period for the control signal 220.

Using the control signal 220 of FIG. 8C, the motor 142 may more subtly transition between the high and low states of fluid flow. That is, the transition between the "pulses" may be tapered so that there may not be a sudden reduction in fluid flow, but a more gradual reduction. In some examples, the peak voltage 222 may be three times as large as the minimum voltage 224. As one example, the peak voltage 222 may be selected at 15V and the minimum voltage 224 may be selected at 3V. In this example, the period of the control signal 220 may be 1800 ms with the high duration T5 being 900 ms and the low duration T6 being 900 ms. Although the control signal 222 shown in FIG. 8C is a sine wave, other waveforms are envisioned, such as combination waveforms (e.g., having characteristics of multiple wave types), elliptical waveforms, and the like. Accordingly, the discussion of any particular waveform is meant as illustrative only.

The massage module 172 may not only vary the pulse rate fluid flow of the oral irrigator, but may also vary an outlet fluid pressure for the oral irrigator. FIG. 9A is a chart illustrating an example outlet pressure of the oral irrigator during clean mode. FIG. 9B is a chart illustrating an example outlet pressure of the oral irrigator during massage mode. With reference first to FIG. 9A, the oral irrigator 100 may pulse rapidly (which may be due to the reciprocating nature of the pump) and the outlet pressure 240 may vary between peaks 242 and valleys 244. As can be seen from the graph in FIG. 9A, each pressure peak 242 may be generally close together with a pressure pulse rate of just over 21 peaks per second. Additionally, the average pressure for the peaks 242 may be 91.8 psi and generally the pressure at the peaks 242 ranges between 91 and 92 psi. The example outlet pressures discussed herein are meant as illustrative only and may be higher or lower based as desired.

With continued reference to FIG. 9A, the output pressure 240 may also drop to the valleys 244, which may hover around 0 psi before the pressure ramps back up extend towards a pressure peak 242. Each of the valleys 244 may occur while the piston 145 in the pump 146 is drawing fluid into the pump chamber before it expels the fluid and are therefore due to the reciprocating nature of the pump 146. Accordingly, in examples where a non-reciprocating pump may be used, the outlet pressure during normal mode may be substantially constant.

With reference now to FIG. 9B, during massage mode, the outlet pressure 250 of the oral irrigator 100 may be lower than during clean mode (shown in FIG. 9A) and may also have non-pulsating periods during which the outlet pressure may be close to or at 0 psi. For example, the outlet pressure 250 may include a high pressure period $T_{high}$ and a low pressure period $T_{low}$. During the high pressure period $T_{high}$, the outlet pressure 250 may include a plurality of pressure peaks 252, as well as ramp peaks 256 that are the pressure peak while the oral irrigator 100 is transitioning between the high pressure period and the low pressure period. Additionally, the outlet pressure 250 may include valleys 254, 258. The first valley 254 may be during the high pressure $T_{high}$ period and may be due to the reciprocating nature of the piston 145, as discussed above with respect to FIG. 9A. The second valley 258 represents the low pressure period between pulses of high pressure. During the low pressure period $T_{low}$, the oral irrigator 100 may output little to no pressure.

As shown in FIG. 9B, in some examples, the oral irrigator 100 may have an average outlet pressure of 85.9 psi during massage mode. As with the clean mode, many other outlet pressures are envisioned and the above examples are meant as illustrative only and not limiting.

Figure 10:
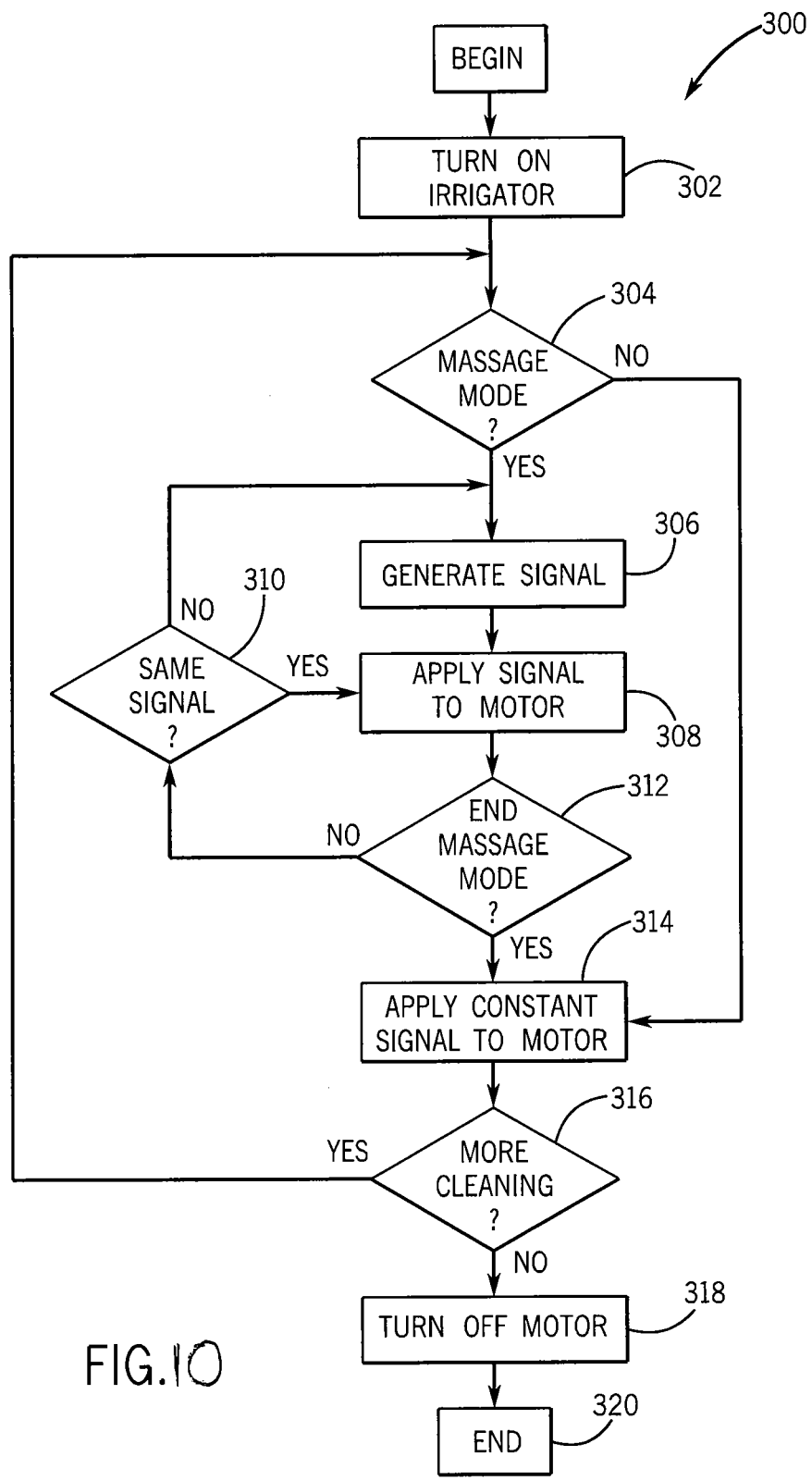
FIG. 10 is a flow chart illustrating a method for operating the oral irrigator including the massage module.

A method for operating the oral irrigator 100 including the massage module 172 will now be discussed in more detail. FIG. 10 is a method 300 for activating the massage mode. The method 300 may begin with operation 302 and the irrigator 100 may be activated. For example, the second control actuator 112 may be selected by a user to turn on the oral irrigator 100. Once the oral irrigator 100 is activated, the method 300 may proceed to operation 304. In operation 304, the processing element 170 may determine whether massage mode has been activated. For example, the processing element 170 may determine whether a user has provided an input to one of the control actuators 110, 112, 124 to select the massage mode. In a specific implementation, the switch 148 may provide an input to the processing element 170 when the second control actuator is activated. As another example, the massage mode may be activated automatically after a select time period of activation of the irrigator 100, e.g., after 30 seconds of operation, the massage mode may be automatically activated.

If the massage mode is not activated, the method may proceed to operation 314, which will be discussed in more detail below. However, if in operation 304 the massage mode is activated, the method 300 may proceed to operation 306. In operation 306, the signal generator 166 may generate a control signal 200, 210, 220. The control signal generated 200, 210, 220 may be selected from a predetermined signal, or as will be discussed in more detail below with respect to FIG. 10, may be generated based on one or more user inputs.

Once the signal generator 166 has generated the control signal 200, 210, 220, the method 300 may proceed to operation 308. In operation 308 the control signal may be applied to the motor. For example, the gate 176 may be activated to provide the control signal from the signal generator 166 to the motor 142. As the control signal is applied to the motor 142, the motor 142 may drive the drive shaft 143 based on the signal. For example, the motor 142 may selectively slow down or stop rotation of the drive shaft and/or may decrease or reduce the torque produced by the drive shaft. The variations in the drive shaft movement may create related changes in the piston 145, thus varying the output of the pump 146, changing the output characteristics of the fluid flow from the tip 114.

After operation 308, the method 300 may proceed to operation 312. In operation 312, the processing element 170 may determine whether to end massage mode. For example, the user may provide a second input to the oral irrigator 100, e.g., by selecting one of the control actuators 110, 112, 124, to indicate that he or she wishes to resume normal mode. As another example, the oral irrigator 100 may have a predetermined time period for massage mode (e.g., 1 minute, or the like), and the processing element 172 may determine to end massage mode once the allotted time has passed.

In operation 312, if massage mode is not terminated, the method 300 may proceed to operation 310. In operation 310, the method 300 may determine whether the same control signal 200, 210, 220 should be applied to the motor or whether a different signal should be applied. If the control signal is to remain the same, the method 300 may return to operation 308 and the signal may continue to be applied to the motor 142. However, in operation 310 if a new signal is desired, the method 300 may return to operation 306 and the signal generator 166 may generate a new control signal. For example, in some examples, a user may wish to vary pressure, pulse rate, or the transition between pulses during massage mode. In these instances, the processing element 170 may receive a user input to vary the control signal and may instruct the signal generator 166 to create a new control signal or vary the current control signal.

With continued reference to FIG. 10, if in operation 312 massage mode is terminated, the method 300 may proceed to operation 314. In operation 314 the processing element 170 may provide a constant signal to the motor 142. In other words, the normal mode signal may be applied to the motor, and in some instances, the normal mode signal may be substantially constant. As the motor 142 receives the normal mode signal, movement of the drive shaft 143 may be constant, and any pulses in the fluid output may be due to the reciprocating nature of the pump 146, rather than variable movement in the motor.

After operation 314, the method 300 may proceed to operation 316. In operation 316, the processing element 170 may determine whether more cleaning is desired. For example, the processing element 170 may determine whether the user has deactivated the power control actuator 112. As another example, the oral irrigator may be configured to have an activation time corresponding to a predetermined "cleaning" length and once the time length has expired, the oral irrigator 100 may automatically shut off.

If more cleaning is desired, the method 300 may return to operation 304. However, if no additional cleaning is desired, the method 300 may proceed to operation 318. In operation 318, the processing element 170 may deactivate the motor. As one example, the processing element 170 may switch off a connection between the power supply 115 and the motor 142. After operation 318, the method 300 may proceed to an end state 320.

Figure 11:
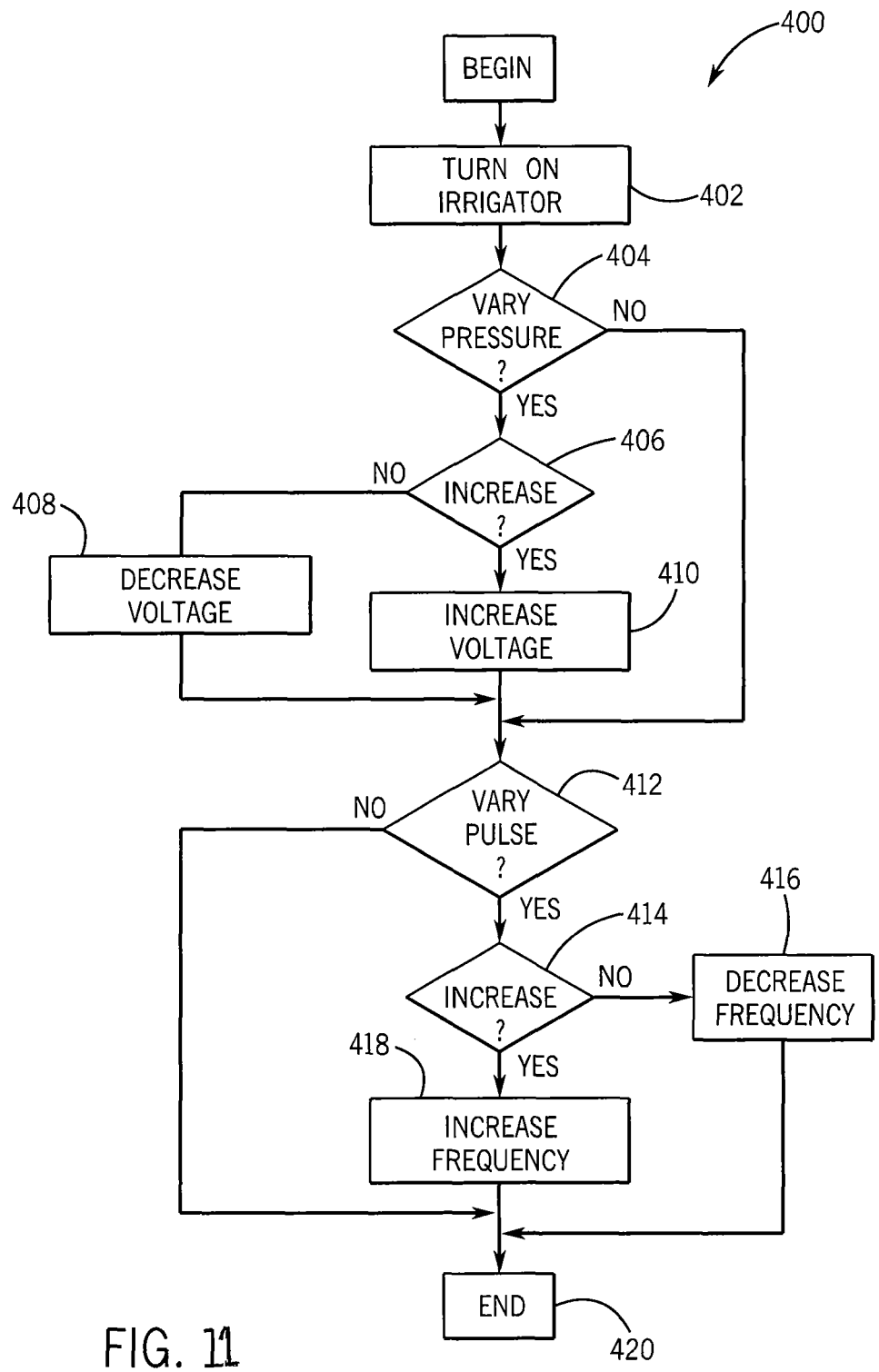
FIG. 11 is a flow chart illustrating a method for dynamically adjusting the pressure and pulse rate of the oral irrigator using the massage module.

In some examples, the pressure and pulse rate of the massage mode may be statically set. However, in other examples, the pressure and pulse rate of the pulses during massage mode may be dynamically modifiable or may be initially set by a user (e.g., calibrated to a particular user's preferences). FIG. 11 is a flow chart illustrating a method for dynamically modifying one or more characteristics of the fluid flow during massage mode. With reference to FIG. 11, the method 400 may begin with operation 402. In operation 402, massage mode for the oral irrigator 100 may be activated. For example, the user may select one of the control actuators 110, 112, 124 to indicate his or her desire to enter massage mode. Once in massage mode, as described in operations 306 and 308 in FIG. 9, the signal generator 166 may generate a signal and apply the signal to the motor 142.

Once massage mode has been activated, the method 400 may proceed to operation 404. In operation 404, the processing element 170 may determine whether the outlet pressure should be varied. For example, on the control actuators 110, 112, 124 may be used to allow the user to provide an input indicating whether he or she wishes for the pressure to be increased or decreased. In a particular example, rotating one of the control actuators 110, 112, 124 in a first direction may correspond to an increase in pressure and rotating in a second direction may correspond to a decrease in pressure.

If the pressure is to be varied from the current control signal output, the method 400 may proceed to operation 406. In operation 406 the processing element 170 may determine whether the pressure should be increased. In other words, the processing element 170 may determine whether the user input to vary the pressure corresponds to an increase in pressure or a decrease. It should be noted that in many implementations, operations 404 and 406 may be performed substantially simultaneously. For example, the processing element 170 may receive a single input that indicates both a change a pressure, as well as whether the pressure is to be increased or decreased.

In operation 406, if the pressure is going to be decreased, the method 400 may proceed to operation 408. In operation 408, the control signal 200, 210, 220 may be modified by the processing element 170 to reduce the maximum voltage 202, 212, 222, or reduce the amplitude of the control signal. As discussed above with respect to FIGS. 8A-8C, by decreasing the maximum voltage of the control signal, the output pressure by the pump 146 may be reduced due to a reduction in output torque by the motor. However, it should be noted that in other examples, the pressure may be decreased manually, such as by a user closing or opening a valve, such a by-pass valve or the like. In these examples, the control signal may not be modified, but the mechanical properties of the fluid path between the reservoir 104 and the tip 114 may be changed.

If in operation 406 the pressure is going to be increased the method 400 may proceed to operation 410. In operation 410, the peak voltage 202, 212, 222 or amplitude of the control signal 200, 210, 220 may be increased. As a specific example, the peak voltage may increase from 10 V to 12V. As discussed above, the outlet pressure may be related to the voltage applied to the motor 142 by the control signal, such that a change in the voltage may correspond to a change in pressure.

After either operation 408 or 410, the method 400 may proceed to operation 412. In operation 412, the processing element 170 may determine whether the pulse length and/or pulse rate should be varied. For example, the user may be provide input to the oral irrigator 100 through one or more of the control actuators 110, 112, 124 indicating his or her desire to increase the pulse rate or length.

If the pulse rate is going to be varied, the method 400 may proceed to operation 414. In operation 414, the processing element 170 may determine whether the pulse rate is going to be increased. For example, the user input to vary the pulse rate may also include an indication of whether the pulse rate should be increased or decreased. Additionally, as discussed above with respect to pressure, in some examples, the user input indicating that the pulse rate should be varied may also include data indicating whether the pulse rate should be increased or decreased.

In operation 414, if the pulse rate is going to decrease, the method 400 may proceed to operation 416. In operation 416, the signal generator 166 may decrease the frequency of the control signal 200, 210, 220. As an example, the duration T1, T2, T3, T4, T5 may be increased, such that the cycles per unit of time of the control signal may be increased, reducing the number of pulses per second.

In operation 414 if the pulse rate is going to be increased, the method 400 may proceed to operation 418. In operation 418, the signal generator 166 may increase the frequency of the control signal. For example, the duration T1, T2, T3, T4, T5 for the control signal may shorten, increasing the number of cycles of the control signal per minute. By shortening the length of the maximum and minimum voltages applied to the motor 142, the length of each pulse may be shortened, increasing the number of pulses per time frame.

After operations 416 or 418 or if in operation 412 the pulse rate is not going to be changed, the method 400 may proceed to an end state 420 and may terminate. It should be noted that the method 400 is an illustrative method for varying one or more characteristics of the fluid flow through the tip 114 during massage mode. However, many other methods are envisioned. As one example, the transition between high and low or fluid flow and a pulse may be varied by changing the transition between the maximum and the minimum voltage levels in the control signal. As another example, the length of fluid flow as compared to pulses or breaks in fluid flow may be varied by changing the duration T1, T2, T3, T4, T5 that either the maximum voltage or the minimum voltage is applied to the motor 142.

Other Examples

As generally discussed above, the processing element 170 may vary a control signal to the motor to change either or both the fluid pulse rate and/or the fluid outlet pressure. In other examples, the processing element 170 may activate a switch or valve to vary the pulse rate and/or pressure. As a first example, the processing element 170 may be in communication with an electrical valve such as a solenoid valve and when the massage mode is activated, the processing element 170 may vary the outlet of the valve to change the pressure and/or may selectively open and close the valve to change the flow rate of the oral irrigator 100. As a second example, the oral irrigator 100 may include a gear driven turbine or a water driven turbine that may be mechanically actuated or actuated by the processing element 170 to vary the flow rate of the oral irrigator 100.

CONCLUSION

The foregoing description has broad application. For example, while examples disclosed herein may focus on a massage mode for oral irrigators, it should be appreciated that the concepts disclosed herein may equally apply to other motor driven devices where a variation in motion may be desired. Similarly, although the massage module is discussed with respect to reducing a pulse rate to create a massage feeling, the devices and techniques disclosed herein are equally applicable to modifying the pulse rate or pressure of an outlet fluid for other applications (e.g., creating a faster pulse rate for quicker or more effective cleaning). Accordingly, the discussion of any example is meant only to be exemplary and is not intended to suggest that the scope of the disclosure, including the claims, is limited to these examples.

Although the present invention has been described with reference to preferred examples, persons skilled in the art will recognize that changes may be made in form and detail without departing from the spirit and scope of the invention. The invention is limited only by the scope of the following claims.

What is claimed is:
1. An oral irrigator comprising:
a reservoir;
a handle including a tip, the handle and tip being in fluid communication with the reservoir;
a pump in fluid communication with the reservoir and the handle;
a motor connected to the pump and configured to selectively actuate the pump; and
a processing element in communication with the motor, wherein upon receiving a user input, the processing element provides either a first control signal or a second control signal to the motor, wherein
the first control signal supplies a constant voltage to the motor;
the second control signal supplies a voltage varying in at least one of magnitude or frequency; and
the application of the first control signal controls a first fluid flow rate over a first time duration cycled at a first pulse rate through the tip or the second control signal controls a second, variable fluid flow rate over a second time duration cycled at a plurality of pulse rates through the tip.
2. The oral irrigator of claim 1, further comprising at least one control actuator in communication with the processing element, wherein when the at least one control actuator is activated, the processing element provides either the first control signal or the second control signal.
3. The oral irrigator of claim 1, wherein the tip is releasable.
4. The oral irrigator of claim 1, wherein the reservoir is connected directly to the handle.

5. The oral irrigator of claim 1, wherein the pump is a reciprocating pump having a pulsed output and each pulse of fluid expelled by the pump has approximately the same volume.

6. An irrigating device comprising:
a pump;
a motor connected to the pump and configured to selectively drive the pump;
a massage mode module in communication with the motor, wherein the massage mode module generates a normal control signal having a constant voltage and a massage control signal having a voltage varying in at least one of magnitude or frequency; wherein
during a normal mode, the massage module provides the normal control signal to the motor causing the pump to cycle at a first pulse rate having a first flow rate over a first time duration; and
during a massage mode, the massage mode module provides the massage control signal to the motor, causing the pump to cycle at variable pulse rate having a second flow rate for a second time duration.

7. The irrigating device of claim 6, wherein the first flow rate is faster than the second flow rate.

8. The irrigating device of claim 7, wherein the first time duration is shorter than the second time duration.

9. The irrigating device of claim 6, wherein the massage control is dynamically adjustable.

10. The irrigating device of claim 6, further comprising a reservoir in fluid communication with the pump; and
a handle including a selectively removable tip, the handle being in fluid communication with the pump; wherein
the first pulse rate and the second pulse rate determine the number of pulses in a fluid flow output by the tip.

11. The irrigating device of claim 6, wherein the massage mode module further comprises a signal generator, wherein the signal generator is configured to produce the massage control signal.

12. The irrigating device of claim 6, wherein the massage control signal includes a maximum voltage and a minimum voltage.

13. The irrigating device of claim 6, wherein during the normal mode the irrigating device has a first outlet pressure and during the massage mode the irrigating device has a second outlet pressure, wherein the second outlet pressure is less than the first outlet pressure.

14. The irrigating device of claim 6, wherein the second flow rate ranges between 50 to 70 percent of the first flow rate.

15. The irrigating device of claim 6, further comprising a control actuator, wherein the control actuator selectively adjusts the massage control system.

16. A method for varying a pulse rate of a liquid deposited into an oral cavity of a user by an oral irrigator comprising
activating a motor connected to pump;
determining by a processing element whether a massage mode should be activated;
if the massage mode is activated, providing a massage signal from the processing element to the motor, causing the pump to cyclically output a massage pulse at a varying pulse rate having a first flow rate over a first time duration; and
if the massage mode is not activated, providing a normal signal from the processing element to the motor, causing the pump to cyclically output a constant pulse rate having a second flow rate over a second time duration; wherein
the normal signal comprises a constant voltage; and
the massage signal comprises a voltage varying in at least one of frequency or magnitude.

17. The method of claim 16, wherein
the massage pulse rate causing a massage fluid pressure; and
the constant pulse rate causing a normal fluid pressure; wherein
the massage fluid pressure is less than the normal fluid pressure.

18. The method of claim 16, determining by the processing element whether the massage mode should be activated further comprises determining whether a user input corresponding to the massage mode has been received.

19. The method of claim 16, wherein the massage signal is generated by a signal generator in communication with the processing element.

20. An oral irrigator comprising:
a reservoir defining a fluid cavity;
a pump in fluid communication with the fluid cavity;
a motor connected to the pump and configured to selectively activate the pump;
a handle in fluid communication with the pump; and
a signal generator in communication with the motor wherein, upon receiving a user input, the signal generator provides either a first control signal supplying a voltage to the motor varying in magnitude, or frequency, or both, to control a first variable fluid flow rate with a plurality of pulse rates over a first time duration or a second control signal supplying a constant voltage to the motor to control a second, constant fluid flow rate with a constant pulse rate over a second time duration.

21. The oral irrigator of claim 20, wherein the reservoir is connected to the handle.

22. The oral irrigator of claim 20, wherein the first control signal corresponds to a first motor speed and the second control signal corresponds to a second motor speed.

23. The oral irrigator of claim 22, wherein the first control signal has a cycle that alternates between a voltage maximum and a voltage minimum.

24. The oral irrigator of claim 23, wherein the cycle determines a pulse rate of the pump.

25. The oral irrigator of claim 22, wherein the first control signal creates a first output pressure and the second control signal creates a second outlet pressure, wherein the second outlet pressure is less than the first outlet pressure.

26. The oral irrigator of claim 25, wherein the first outlet pressure ranges between 90 to 96 psi and the second outlet pressure ranges between 80 to 87 psi.

27. The oral irrigator of claim 20, wherein the first control signal is one of a sine wave or a square wave.

* * * * *